United States Patent
Konobe et al.

(10) Patent No.: US 12,232,892 B2
(45) Date of Patent: Feb. 25, 2025

(54) DEVICE FOR DISPLAYING BLOOD-PRESSURE-RELATED INFORMATION, METHOD FOR DISPLAYING BLOOD-PRESSURE-RELATED INFORMATION, AND COMPUTER-READABLE RECORDING MEDIUM

(71) Applicant: OMRON HEALTHCARE CO., LTD., Muko (JP)

(72) Inventors: Sayuri Konobe, Kyoto (JP); Shingo Yamashita, Kyoto (JP)

(73) Assignee: OMRON HEALTHCARE CO., LTD., Muko (JP)

( * ) Notice: Subject to any disclaimer, the term of this patent is extended or adjusted under 35 U.S.C. 154(b) by 99 days.

(21) Appl. No.: 18/072,128

(22) Filed: Nov. 30, 2022

(65) Prior Publication Data
US 2023/0089660 A1    Mar. 23, 2023

Related U.S. Application Data

(63) Continuation of application No. PCT/JP2021/025463, filed on Jul. 6, 2021.

(30) Foreign Application Priority Data

Jul. 28, 2020  (JP) .................................. 2020-127479

(51) Int. Cl.
*A61B 5/00*    (2006.01)
*A61B 5/021*   (2006.01)
(Continued)

(52) U.S. Cl.
CPC .............. *A61B 5/743* (2013.01); *A61B 5/021* (2013.01); *A61B 5/7475* (2013.01);
(Continued)

(58) Field of Classification Search
CPC ................................ A61B 5/743; A61B 5/021
See application file for complete search history.

(56) References Cited

U.S. PATENT DOCUMENTS 4,747,412 A * 5/1988 Yamaguchi ............ A61B 5/022
                                                       600/495
6,190,694 B1 * 2/2001 Mizushima .......... A61K 9/4858
                                                       424/450
(Continued)

FOREIGN PATENT DOCUMENTS

JP    2010-82009 A    4/2010
JP    2015-216970 A   12/2015
(Continued)

OTHER PUBLICATIONS

Sep. 7, 2021 International Search report issued in Patent Application No. PCT/JP2021/025463.
(Continued)

*Primary Examiner* — Yi Yang
(74) *Attorney, Agent, or Firm* — Oliff PLC

(57) ABSTRACT

In the present invention, date and time are set in a horizontal direction and blood pressure is set in a vertical direction on a display screen, and a change in a blood pressure value over a display target period is displayed as a bar graph with vertical bars each formed by connecting SBP and DBP for each time and arranged in the horizontal direction. When a position corresponding to a vertical bar at a specific time on the display screen is designated with a pointing device, blood pressure value data measured for each day at the specific time are averaged over the display target period to obtain a systolic blood pressure average value and/or a diastolic blood pressure average value, according to the position designated. The obtained systolic blood pressure average value and/or diastolic blood pressure average value (Continued)

is displayed together with the bar graph on the display screen.

15 Claims, 29 Drawing Sheets

(51) Int. Cl.
  *G06T 11/20* (2006.01)
  *G16H 40/67* (2018.01)
  *G06F 3/04845* (2022.01)
  *G06F 3/0488* (2022.01)

(52) U.S. Cl.
  CPC .......... *G06T 11/206* (2013.01); *G16H 40/67* (2018.01); *G06F 3/04845* (2013.01); *G06F 3/0488* (2013.01); *G06F 2203/04808* (2013.01); *G06T 2200/24* (2013.01); *G06T 2210/41* (2013.01)

(56) References Cited

U.S. PATENT DOCUMENTS

| | | | |
|---|---|---|---|
| 2012/0109688 A1* | 5/2012 | Yoo | G16H 40/67 705/3 |
| 2017/0098318 A1* | 4/2017 | Iannaccone | G06F 3/04855 |
| 2018/0176965 A1* | 6/2018 | Mathias | G06F 3/02 |
| 2018/0310837 A1* | 11/2018 | Yamashita | A61B 5/7435 |
| 2019/0279229 A1* | 9/2019 | Warita | G06Q 30/06 |

FOREIGN PATENT DOCUMENTS

| | | |
|---|---|---|
| JP | 2016-182248 A | 10/2016 |
| WO | 2019/230494 A1 | 12/2019 |

OTHER PUBLICATIONS

Jan. 31, 2023 International Preliminary Report on Patentability issued in International Patent Application No. PCT/JP2021/025463.

\* cited by examiner

DEVICE FOR DISPLAYING BLOOD-PRESSURE-RELATED INFORMATION, METHOD FOR DISPLAYING BLOOD-PRESSURE-RELATED INFORMATION, AND COMPUTER-READABLE RECORDING MEDIUM

CROSS-REFERENCE TO RELATED APPLICATION

This application is based on an application No. 2020-127479 filed in Japan on Jul. 28, 2020, the entire content of which is hereby incorporated by reference.

TECHNICAL FIELD

The present invention relates to a device for displaying blood-pressure-related information and a method for displaying blood-pressure-related information that display information related to blood pressure of a subject on a display screen. The present invention relates to a computer-readable recording medium storing a program for causing a computer to execute such a method for displaying blood-pressure-related information.

BACKGROUND ART

Conventionally, as this type of device for displaying blood-pressure-related information, for example, one disclosed in Patent Literature 1 (Japanese Patent Application Laid-Open No. 2015-216970) is known. The hospital terminal constituting the device for displaying blood-pressure-related information displays, on the display screen, a blood pressure evaluation item list for prompting a doctor to select a blood pressure evaluation item. When an item of "blood pressure value transition (displayed for 90 days)", for example, is selected in the blood pressure evaluation item list, the transition of the systolic blood pressure value (SBP) and the diastolic blood pressure value (DBP) measured in the morning, in the evening, and at night for 90 days backward from the consultation day of this time is displayed on the display screen as a line graph (see FIG. 7 of the same Literature). When an item of "period average value (comparison between last time and this time)" is selected in the blood pressure evaluation item list, a period average value of the blood pressure values measured in the evening, at night, and in the morning in the consultation period of this time (period from the consultation of the last the time to the consultation of this time) is compared with a period average value of the blood pressure values measured in the evening, at night, and in the morning in the consultation period of the last time (period from the consultation of the last but one to the consultation of the last time), and displayed on the display screen as a bar graph (see FIG. 8 of the same Literature).

SUMMARY OF INVENTION

Recently, the relationship between blood pressure variation at night and a cardiovascular risk has attracted attention, and blood pressure measurement is sometimes performed at a predetermined plurality of times (for example, 2:00 AM, 3:00 AM, 4:00 AM, and the like) at night. In this case, there is a need to easily know the blood pressure average value over a plurality of days for a specific time.

However, in the device for displaying blood-pressure-related information of the conventional example, even if blood pressure measurement is performed at a plurality of times at night, the blood pressure value data measured at the plurality of times are not distinguished from one another for each time, and there is a problem that the blood pressure average value in which the blood pressure values at the plurality of times are put together is calculated (displayed).

Therefore, an object of the present invention is to provide a device for displaying blood-pressure-related information and a method for displaying blood-pressure-related information capable of displaying a blood pressure average value over a plurality of days at a specific time on a display screen by a simple operation. An object of the present invention is to provide a computer-readable recording medium storing a program for causing a computer to execute such a method for displaying blood-pressure-related information.

In order to achieve the object, a device for displaying blood-pressure-related information of the present disclosure is a device that displays information related to blood pressure of a subject on a display screen, the device comprising:

a data input unit that receives, for a subject, blood pressure value data including a systolic blood pressure value and a diastolic blood pressure value measured at least at a predetermined plurality of times of a day for each day over a plurality of days;

a storage unit that is capable of storing the blood pressure value data;

a pointing device that is capable of operation of designating a position on the display screen;

an initial display control unit that sets date and time in a horizontal direction and blood pressure in a vertical direction on the display screen, and displays, as a bar graph, a change in a blood pressure value over a display target period corresponding to all or some of the plurality of days with vertical bars each formed by connecting the systolic blood pressure value and the diastolic blood pressure value for each time and arranged in a horizontal direction;

a first calculation unit that, when a position corresponding to a vertical bar at a specific time on the display screen is designated with the pointing device during display of the bar graph, averages data of the systolic blood pressure value measured for each day at the specific time over the display target period to obtain a systolic blood pressure average value for the specific time, and/or averages data of the diastolic blood pressure value measured for each day at the specific time over the display target period to obtain a diastolic blood pressure average value for the specific time, according to the position designated; and a first display control unit that displays, on the display screen, the systolic blood pressure average value and/or the diastolic blood pressure average value obtained for the specific time together with the bar graph.

In the present description, "time" in "a predetermined plurality of times of a day" means a daily time, that is, a time for which a date is not considered. For example, the "time" at which the blood pressure value is measured refers to 2:00 AM, 4:00 AM, and the like, but is not limited to this. The "time" may include a time relatively set as, for example, "x hours since bedding down" (for example, x=4).

The "plurality of days" typically refers to a period such as two weeks or one month.

The "blood pressure value data" includes the systolic blood pressure value and the diastolic blood pressure value.

Other than them, data of the pulse rate measured together with the blood pressure value may be included.

An initial display control unit "sets~in the horizontal direction and sets~in the vertical direction" means that corresponding amounts (date and time, blood pressure, and the like) are set as the horizontal axis and the vertical axis, respectively, in a state where the user (the subject and medical personnel such as a doctor or a nurse) views the display screen. However, an axis (straight line), a scale, and the like are not necessarily displayed on the display screen.

A "display target period" is a period presented in the horizontal direction on the display screen, and typically refers to a period such as several days or one week.

A "pointing device" is a device for a user to perform an operation of designating a position on the display screen, and may be a mouse, a touchpad placed on the display screen (the user designates a position on the pad with a finger or a pen), or the like.

Assuming that the display target period is n days (n is a natural number) and the blood pressure values at the specific time are BP1, BP2, . . . , and BPn, the "blood pressure average value" over the display target period is defined by (BP1+BP2+ . . . +BPn)/n (in the present description, this definition is extended to the case of n=1).

"The systolic blood pressure average value and/or the diastolic blood pressure average value" means a blood pressure average value of any one of the systolic blood pressure average value and the diastolic blood pressure average value, or blood pressure average values of the both.

In another aspect, a method for displaying blood-pressure-related information of the present disclosure is a method for displaying blood-pressure-related information for displaying information related to blood pressure of a subject on a display screen, comprising:
   a storage unit that is capable of storing blood pressure value data including a systolic blood pressure value and a diastolic blood pressure value;
   a calculation unit that is capable of calculating the blood pressure value data; and
   a pointing device that is capable of performing operation of designating a position on the display screen,
   the method for displaying blood-pressure-related information comprising:
   receiving, for a subject, the blood pressure value data measured at a predetermined plurality of times of a day for each day over a plurality of days, and causing the storage unit to store the blood pressure value data;
   setting date and time in a horizontal direction and blood pressure in a vertical direction on the display screen, and displaying, as a bar graph, a change in a blood pressure value over a display target period corresponding to all or some of the plurality of days with vertical bars each formed by connecting the systolic blood pressure value and the diastolic blood pressure value for each time and arranged in a horizontal direction;
   averaging, when a position corresponding to a vertical bar at a specific time on the display screen is designated with the pointing device during display of the bar graph, data of the systolic blood pressure value measured for each day at the specific time over the display target period to obtain a systolic blood pressure average value for the specific time, and/or averaging data of the diastolic blood pressure value measured for each day at the specific time over the display target period to obtain a diastolic blood pressure average value for the specific time, according to the position designated; and
   displaying, on the display screen, the systolic blood pressure average value and/or the diastolic blood pressure average value obtained for the specific time together with the bar graph.

In yet another aspect, a computer-readable recording medium according to the present disclosure is a non-transitorily computer-readable recording medium storing a program for causing a computer to execute the above method for displaying blood-pressure-related information.

In another aspect, a device for displaying blood-pressure-related information of the present disclosure is a device for displaying blood-pressure-related information that displays information related to blood pressure of a subject on a display screen, the device comprising:
   a data input unit that receives, for a subject, blood pressure value data including a systolic blood pressure value and a diastolic blood pressure value measured at least at a predetermined plurality of times of a day for each day over a plurality of days;
   a storage unit that is capable of storing the blood pressure value data;
   a pointing device that is capable of operation of designating a position on the display screen;
   an initial display control unit that sets date and time in a horizontal direction and blood pressure in a vertical direction on the display screen, and displays a change in a blood pressure value over a display target period corresponding to all or some of the plurality of days as an SBP line graph in which points each corresponding to the systolic blood pressure value are connected by line segments and a DBP line graph in which points each corresponding to the diastolic blood pressure value are connected by line segments;
   a first calculation unit that, when a position corresponding to a specific time on the SBP line graph is designated with the pointing device during display of the line graph, averages data of the systolic blood pressure value measured for each day at a specific time over the display target period to obtain a systolic blood pressure average value for the specific time according to the position designated, and/or, when a position corresponding to a specific time on the DBP line graph is designated with the pointing device during display of the line graph, averages data of the diastolic blood pressure value measured for each day at the specific time over the display target period to obtain a diastolic blood pressure average value for the specific time according to the position designated; and
   a first display control unit that displays, on the display screen, the systolic blood pressure average value and/or the diastolic blood pressure average value obtained for the specific time together with the line graph.

BRIEF DESCRIPTION OF DRAWINGS

The present invention will become more fully understood from the detailed description given hereinbelow and the accompanying drawings which are given by way of illustration only, and thus are not limitative of the present invention, and wherein.

DESCRIPTION OF EMBODIMENTS

An embodiment of the present invention will be described below in detail with reference to the drawings.

(Configuration of System)

Figure 1:
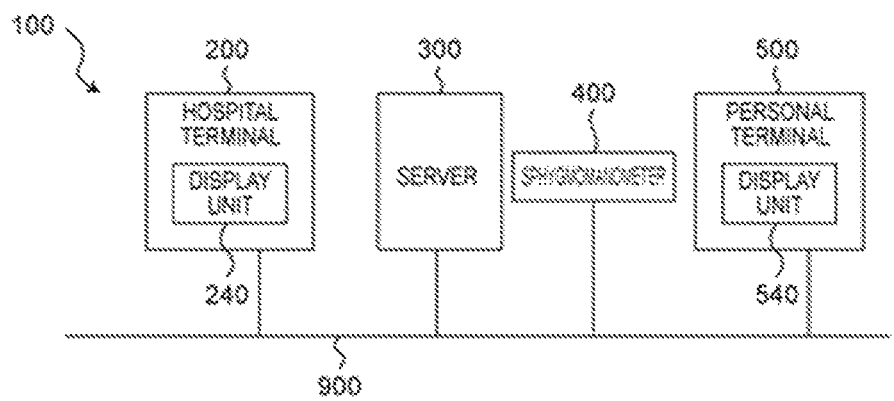
FIG. 1 is a block diagram illustrating one embodiment in which the device for displaying blood-pressure-related information of the present invention is configured as a system on a network.

FIG. 1 illustrates an example in which the device for displaying blood-pressure-related information of the present invention is configured as a system (the entirety is denoted by reference sign 100) of one embodiment on a network. The system 100 includes a hospital terminal 200 having a display unit 240 as a display screen, a server 300, a sphygmomanometer 400, and a personal terminal 500 having a display unit 540 as a display screen. The hospital terminal 200, the server 300, the sphygmomanometer 400, and the personal terminal 500 can communicate with one another via a network 900.

Figure 2:
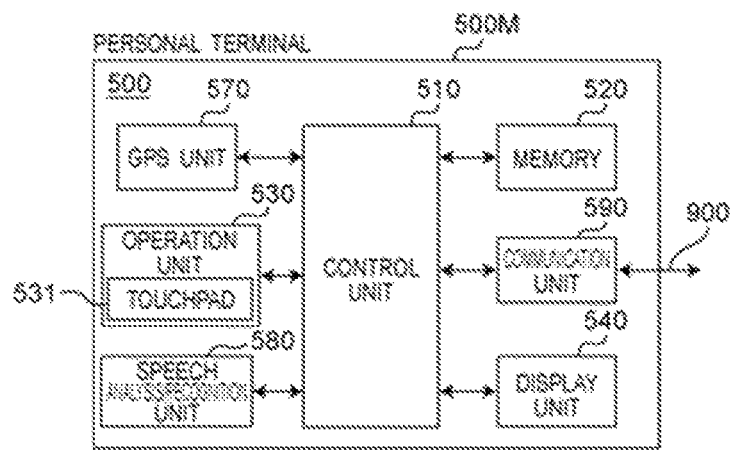
FIG. 2 is a block diagram illustrating a configuration of a personal terminal included in the system.

As illustrated in FIG. 2, the personal terminal 500 includes a main body 500M, and a control unit 510, a memory 520, an operation unit 530, a display unit 540 as a display screen, a global positioning system (GPS) unit 570, a speech analysis/recognition unit 580, and a communication unit 590 that are mounted on the main body 500M. The personal terminal 500 includes a commercially available smartphone, has application software (computer program) installed therein so as to perform processing described later, and can access the server 300.

The control unit 510 includes a central processing unit (CPU) and its auxiliary circuit, controls each unit of the personal terminal 500, and executes processing described later according to a program and data stored in the memory 520. That is, the control unit 510 processes data input from the operation unit 530 and the communication unit 590, and causes the processed data to be stored in the memory 520, to be displayed on the display unit 540, or to be output from the communication unit 590.

The memory 520 includes a random access memory (RAM) used as a work area necessary for the control unit 510 to execute a program, and a read only memory (ROM) for storing a basic program to be executed by the control unit 510. As a storage medium of an auxiliary storage device for assisting a storage area of the memory 520, a semiconductor memory (a memory card and a solid state drive (SSD)) or the like may be used.

In this example, the operation unit 530 includes a touch-pad 531 superimposed on the display screen of the display unit 540 and a hardware switch not illustrated, and inputs, to the control unit 510, an operation signal indicating operation by the user (in this example, a subject).

The display unit 540 includes a display screen (for example, a liquid crystal display (LCD), an electroluminescence (EL) display, or the like). The display unit 540 is controlled by the control unit 510 to display a predetermined picture on the display screen. In this example, the display unit 540 and the touchpad 531 constitute a known touchscreen.

The GPS unit 570 includes a known system, receives signals from several satellites in the sky, and calculates the current position of the personal terminal 500. The calculated current positions are sequentially recorded in the memory 520.

The speech analysis/recognition unit 580 includes known Siri (registered trademark) (speech interpretation and recognition interface), and is used to recognize, analyze, and input speech from the user in this example.

The communication unit 590 transmits information from the control unit 510 to another device (in this example, the server 300) via the network 900. The communication unit 590 receives information from another device via the network 900 and passes it to the control unit 510.

Figure 3:
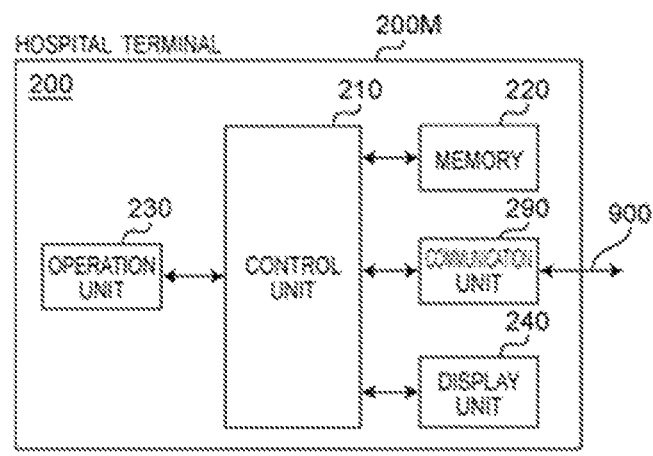
FIG. 3 is a block diagram illustrating a configuration of a hospital terminal included in the system.

As illustrated in FIG. 3, the hospital terminal 200 includes a main body 200M, a control unit 210, a memory 220, an operation unit 230, a display unit 240 as a display screen, and a communication unit 290 that are mounted on the main body 200M. The hospital terminal 200 includes a commercially available laptop personal computer, has a computer program installed therein similar to that in the personal terminal 500, and can access the server 300.

The control unit 210 and the memory 220 are configured similarly to the control unit 510 and the memory 520 in the personal terminal 500, respectively.

In this example, the operation unit 230 includes a keyboard and a mouse, and inputs, to the control unit 210, an operation signal indicating operation by the user (in this example, a doctor). The operation unit 230 may include another operation device such as a touchscreen instead of or in addition to the keyboard and the mouse.

The display unit 240 includes a display screen (for example, an LCD, an EL display, or the like). The display unit 240 is controlled by the control unit 210 to display a predetermined picture on the display screen.

The communication unit 290 transmits information from the control unit 210 to another device (in this example, the server 300) via the network 900. The communication unit 290 receives information from another device via the network 900 and passes it to the control unit 210.

Figure 4:
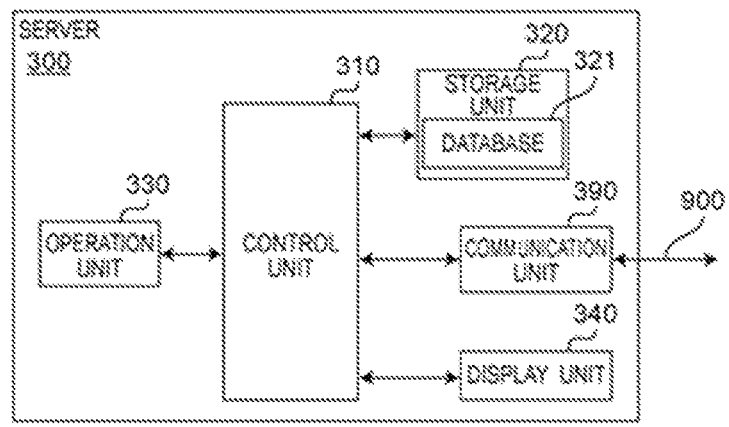
FIG. 4 is a block diagram illustrating a configuration of a server included in the system.

As illustrated in FIG. 4, the server 300 includes a control unit 310, a storage unit 320, an operation unit 330, a display unit 340, and a communication unit 390. The server 300 is a general-purpose computer device having a computer program installed therein to cause the general-purpose computer device to perform predetermined processing.

The control unit 310 includes a CPU and its auxiliary circuit, controls each unit of the server 300, executes predetermined processing according to a program and data stored in the storage unit 320, processes data input from the operation unit 330 and the communication unit 390, and causes the processed data to be stored in the storage unit 320, to be displayed on the display unit 340, or to be output from the communication unit 390.

The storage unit 320 includes a RAM used as a work area necessary for the control unit 310 to execute a program, and a ROM for storing a basic program to be executed by the control unit 310. The storage unit 320 is provided with a database 321 including blood pressure value data sent from many subjects. As a storage medium of an auxiliary storage device for assisting a storage area of the storage unit 320, a magnetic disk (a hard disk (HD) and a flexible disk (FD)), an optical disk (a compact disc (CD) and a digital versatile disk (DVD), and a Blu-ray (registered trademark) disc (BD)), a magneto-optical disk (MO), a semiconductor memory (a memory card and an SSD), or the like may be used.

In this example, the operation unit 330 includes a keyboard and a mouse, and inputs, to the control unit 310, an operation signal indicating operation by the user. The operation unit 330 may include another operation device such as a touchscreen instead of or in addition to the keyboard and the mouse.

The display unit 340 includes a display screen (for example, an LCD, an EL display, or the like). The display unit 340 is controlled by the control unit 310 to display a predetermined picture on the display.

The communication unit 390 transmits information from the control unit 310 to another device (in this example, the personal terminal 500 and the hospital terminal 200) via the network 900. The communication unit 390 receives information from another device via the network 900 and passes it to the control unit 310.

Figure 5:
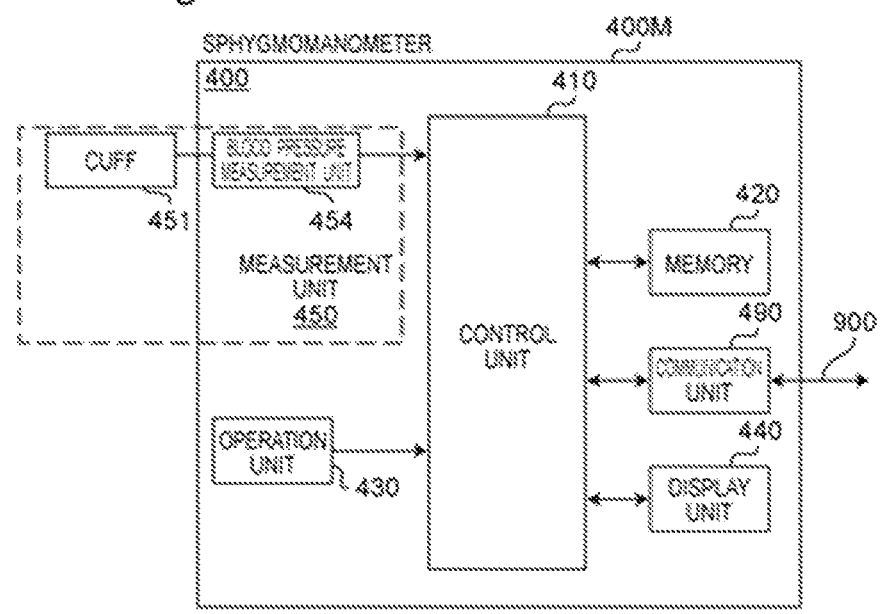
FIG. 5 is a block diagram illustrating a configuration of a sphygmomanometer included in the system.

As illustrated in FIG. 5, the sphygmomanometer 400 includes a casing 400M, and a control unit 410, a memory 420, an operation unit 430, a display unit 440, a measurement unit 450 as a blood pressure data acquisition unit, and a communication unit 490 that are mounted on the casing 400M.

In response to operation by an operator on an operation device (not illustrated) such as an operation button or an operation key, the operation unit 430 inputs an operation signal corresponding to the content of the operation to the control unit 410.

The measurement unit 450 includes a cuff 451 for measuring blood pressure and a blood pressure measurement unit 454, and acquires, from a subject, systolic blood pressure (SBP), which is the maximum blood pressure, diastolic blood pressure (DBP), which is the minimum blood pressure, and a measurement value of pulse rate in association with measurement date and time. Hereinafter, the systolic blood pressure value (SBP) and the diastolic blood pressure value (DBP) as blood pressure value data, the pulse rate, the measurement date and time, and the like are collectively referred to as blood-pressure-related data.

The memory 420 stores data of a program for controlling the sphygmomanometer 400, setting data for setting various functions of the sphygmomanometer 400, data of a measurement result, and the like. The memory 420 is used as a work memory or the like when the program is executed.

The control unit 410 includes a CPU, and controls the memory 420, the display unit 440, and the communication unit 490 based on a detection signal from the measurement unit 450 in response to an operation signal from the operation unit 430 according to the program for controlling the sphygmomanometer 400 stored in the memory 420. The control unit 410 includes a schedule unit, and the schedule unit can execute a mode (referred to as schedule mode or a night measurement mode) of automatically measuring blood pressure at one or a predetermined plurality of times of a day in addition to a mode of measuring blood pressure when a "measurement" instruction is input by the operation unit 430. Here, the "time" in "one or a predetermined plurality of times of a day" means a daily time, that is, a time for which a date is not considered. For example, the "time" at which the blood pressure value is measured refers to, for example, 2:00 AM, 4:00 AM, and the like at night, but is not limited to this. The "time" may include a time relatively set as, for example, "x hours since bedding down" (for example, x=4).

The display unit 440 includes a display and an indicator, and displays predetermined information according to a control signal from the control unit 410.

Controlled by the control unit 410, the communication unit 490 transmits predetermined information to another device (in this example, the server 300) via the network 900. The communication unit 490 receives information from another device via the network 900 and passes it to the control unit 410. Communication via the network 900 may be either wireless or wired.

The network 900 is the Internet in this example, but is not limited to this, and may be another type of network such as a hospital local area network (LAN), or may be one-to-one communication using a universal serial bus (USB) cable or the like.

(Schematic Operation of System)

The system 100 is generally used as follows.

i) Using the sphygmomanometer 400, the subject automatically measures his/her blood pressure, for example, at home for each day over a plurality of days at one or a predetermined plurality of times t1, t2, and t3 in one day. In this example, the time t1 is 2:00 AM, the time t2 is 4 hours since bedding down, and the time t3 is 4:00 AM. The reason for this is because the blood pressure at these times t1, t2, and t3 has recently attracted attention in relation to cardiovascular risk. Here, "4 hours since bedding down" for the time t2 means a time relatively set as 4 hours since bedding down. For example, if the time when the subject goes to bed is 11:00 PM, 4 hours since bedding down corresponds to 3:00 AM. If the time when the subject goes to bed varies from day to day, the time t2 also varies accordingly. When measurement ends, the sphygmomanometer 400 transmits, each time of the measurement, the blood-pressure-related data including the measured systolic blood pressure value (SBP), the diastolic blood pressure value (DBP), the pulse rate, and the measurement date and time to the server 300 via the network 900.

In this example, it is assumed that the daily blood pressure measurement by the subject is sequentially performed for one month.

ii) The server 300 receives the blood-pressure-related data from the sphygmomanometer 400 via the communication unit 390 functioning as a data input unit. Then, the server 300 causes the storage unit 320 (in particular, the database 321) to store the received blood-pressure-related data with distinguished for each subject.

iii) In this example, the personal terminal 500 is operated by a user who is a subject. Specifically, the user operates the operation unit 530, accesses the database 321 of the server 300, and downloads the user's blood-pressure-related data for one month via the communication unit 590. The downloaded blood-pressure-related data is stored in the memory 520 as a storage unit. In this example, the method for displaying blood-pressure-related information described later is executed by the control unit 510 of the personal terminal 500 based on the stored blood-pressure-related data.

iv) In this example, the hospital terminal 200 is operated by a doctor who examines the subject. Specifically, the doctor operates the operation unit 230, accesses the database 321 of the server 300, and downloads the subject's blood-pressure-related data for one month via the communication unit 290. The downloaded blood-pressure-related data is stored in the memory 220 as a storage unit. In this example, the method for displaying blood-pressure-related information described later can be executed also by the control unit 210 of the hospital terminal 200 based on the stored blood-pressure-related data. However, in the following example, for the sake of simplicity, it is assumed that the user who is the subject executes the method for displaying blood-pressure-related information using the personal terminal 500.

(Method for Displaying Blood-Pressure-Related Information)

Figure 6A:
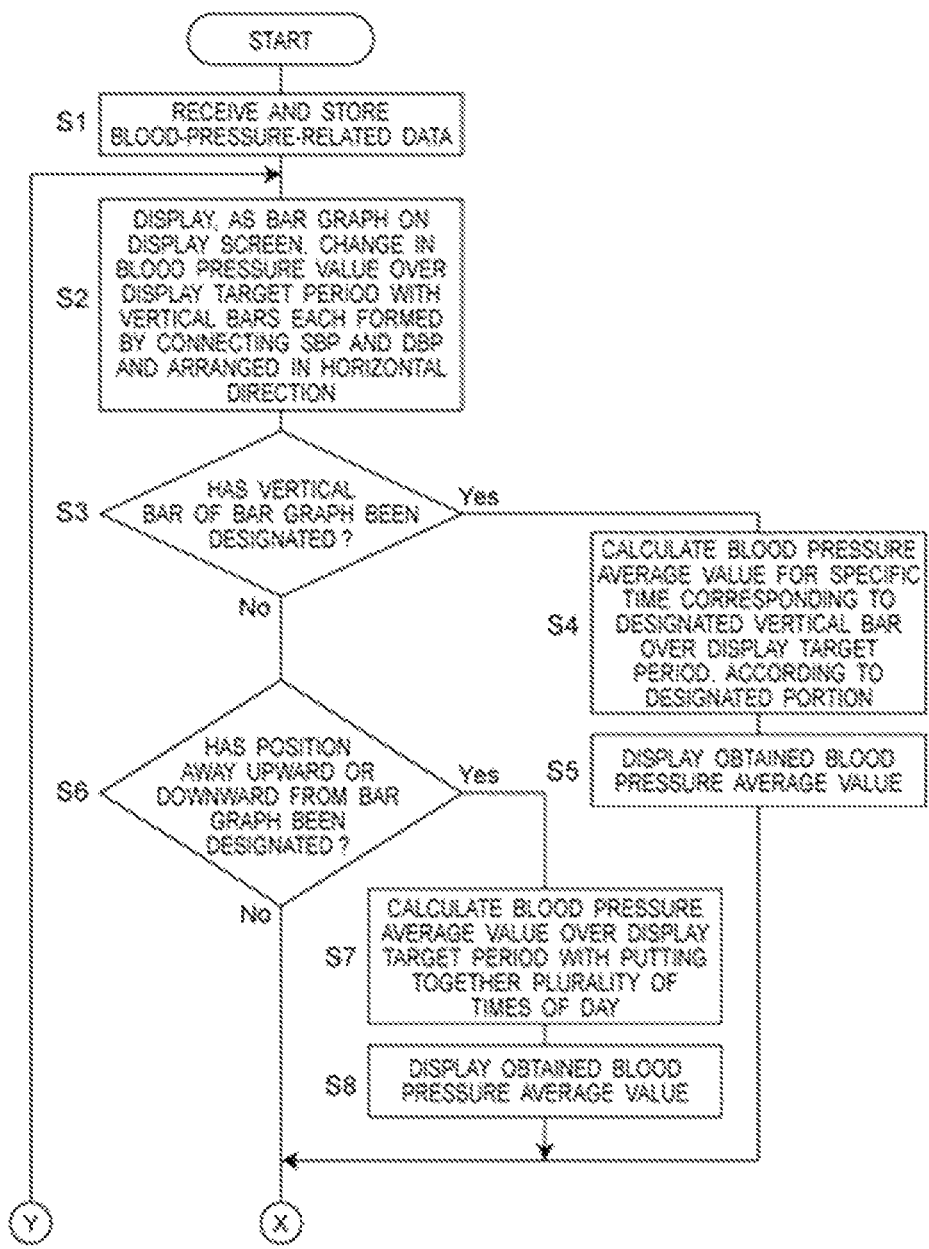
FIG. 6A is a view illustrating a part of an operation flow by a control unit of the personal terminal.
Figure 6B:
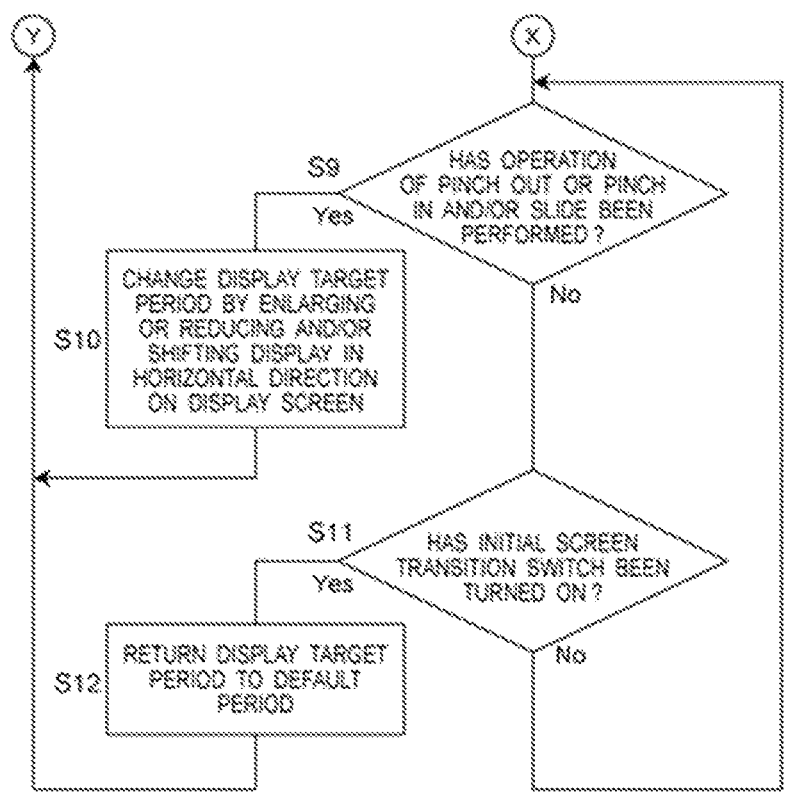
FIG. 6B is a view illustrating a rest part of the operation flow by the control unit of the personal terminal.

FIGS. 6A and 6B illustrate an operation flow by the control unit 510 of the personal terminal 500 when the user who is the subject executes the method for displaying blood-pressure-related information using the personal terminal 500.

First, in step S1 of FIG. 6A, the control unit 510 receives the subject's blood-pressure-related data for one month via the communication unit 590, and stores the data in the memory 520 as a storage unit. As described above, the blood-pressure-related data includes the systolic blood pressure value (SBP), the diastolic blood pressure value (DBP), the pulse rate, and the measurement date and time as the blood pressure value data.

Figure 7:
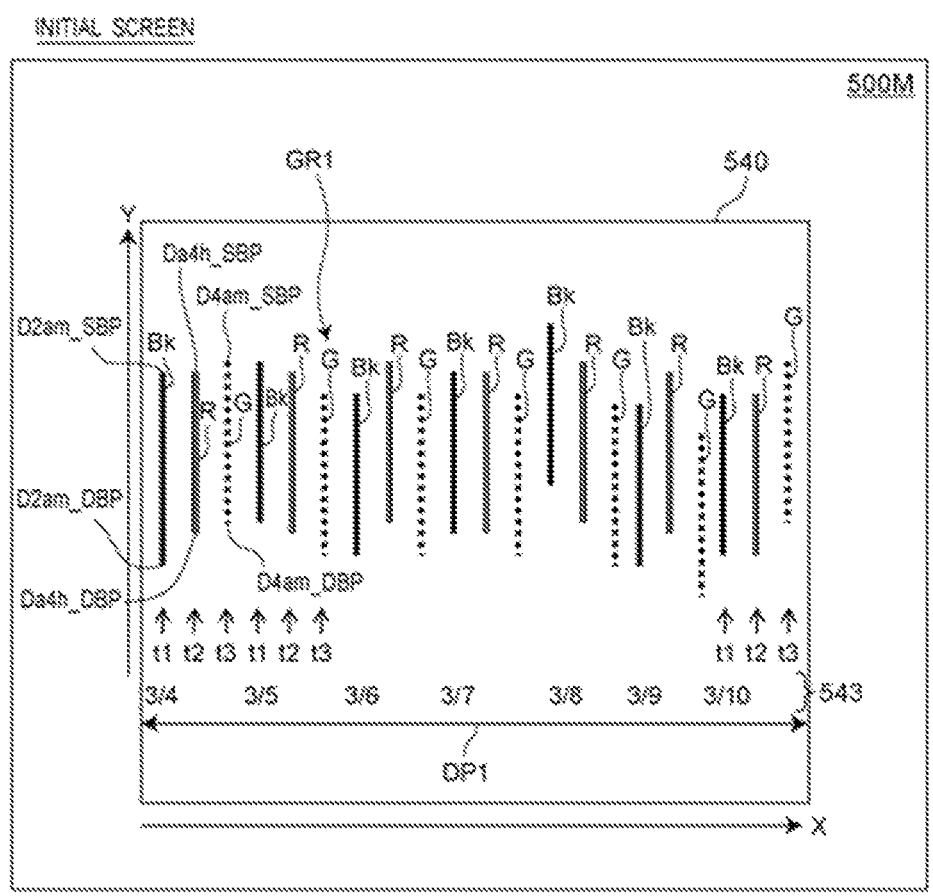
FIG. 7 is a view exemplifying an initial screen displayed on a display unit of the personal terminal.

Next, in step S2 of FIG. 6A, the control unit 510 acts as an initial display control unit, and displays an initial screen as exemplified in FIG. 7 on the display unit 540. In this initial screen, the date and time are set in a horizontal direction X, and the blood pressure is set in a vertical direction Y. In the horizontal direction X, dates from March 4 to March 10 are displayed in an area (date display area) 543 along the lower side of the display unit 540. As known from this date display, in the initial screen, the length of a display target period DP1 is set by default to seven days corresponding to a part of the one month in which the blood-pressure-related data was measured. On the other hand, in the vertical direction Y, a scale or the like indicating the blood pressure value is not particularly displayed. A change in the blood pressure value over the display target period DP1 is displayed as a bar graph GR1 substantially at the center of the display unit 540. The bar graph GR1 is created by connecting the SBP and the DBP for each of the measured times t1, t2, and t3 to form the vertical bars Bk, R, and G, and arranging the vertical bars Bk, R, and G in the horizontal direction X. Specifically, the vertical bar Bk is created by connecting the SBP (represented by reference sign "D2am_SBP") at the time t1 and the DBP (represented by reference sign "D2am_DBP") at the time t1. The vertical bar R is created by connecting the SBP (represented by reference sign "Da4h_SBP") at the time t2 and the DBP (represented by reference sign "Da4h_DBP") at the time t2. The vertical bar G is created by connecting the SBP (represented by reference sign "D4am_SBP") at the time t3 and the DBP (represented by reference sign "D4am_DBP") at the time t3. Due to this, the bar graph GR1 represents a change in the SBP and a change in the DBP over the display target period DP1.

In the example of FIG. 7 (and FIGS. 8 to 23, 25, 26, 28, and 29 described later), the vertical bars Bk, R, and G are indicated by a solid line, a double line, and a broken line, respectively, in order to be distinguished from one another. In this example, the vertical bars Bk, R, and G are color-coded into black, red, and green, respectively, in order to be distinguished from one another. This allows the user to easily identify the vertical bars Bk, R, and G constituting the bar graph GR2 on the display unit 540 for each daily time corresponding to each of the vertical bars Bk, R, and G. Note that the colors, line types, and thicknesses of the vertical bars Bk, R, and G can be discretionarily set.

Figure 8:
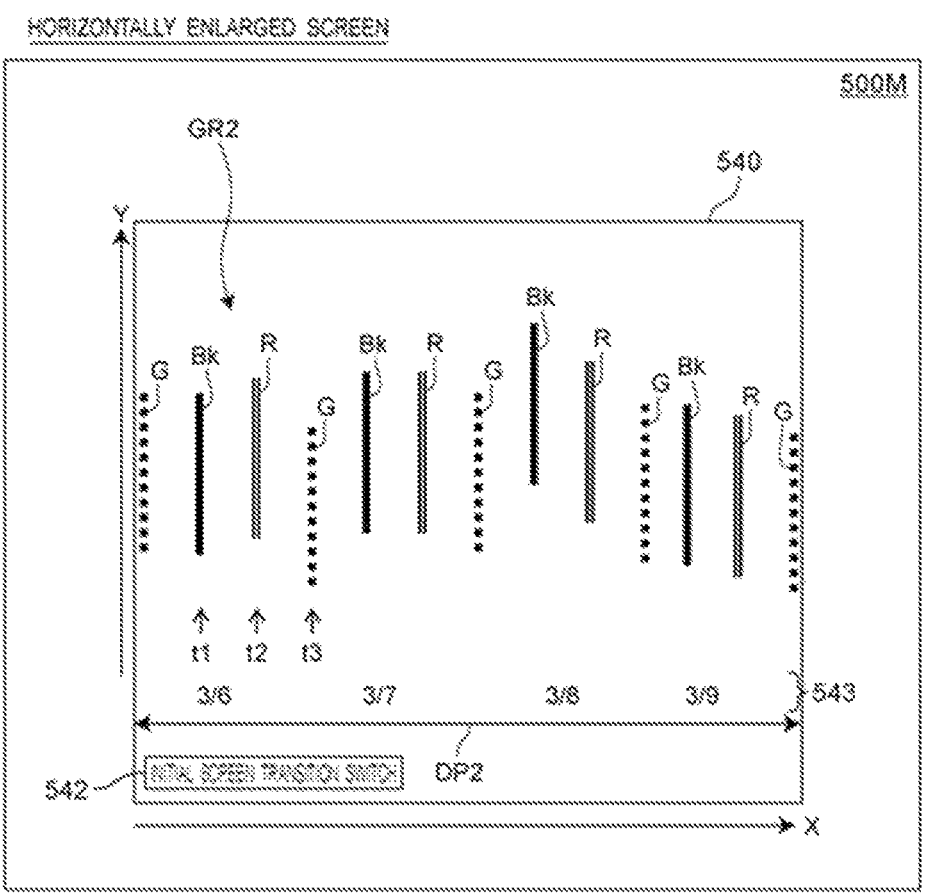
FIG. 8 is a view exemplifying a screen in a state where the initial screen is enlarged in a horizontal direction.
Figure 9:
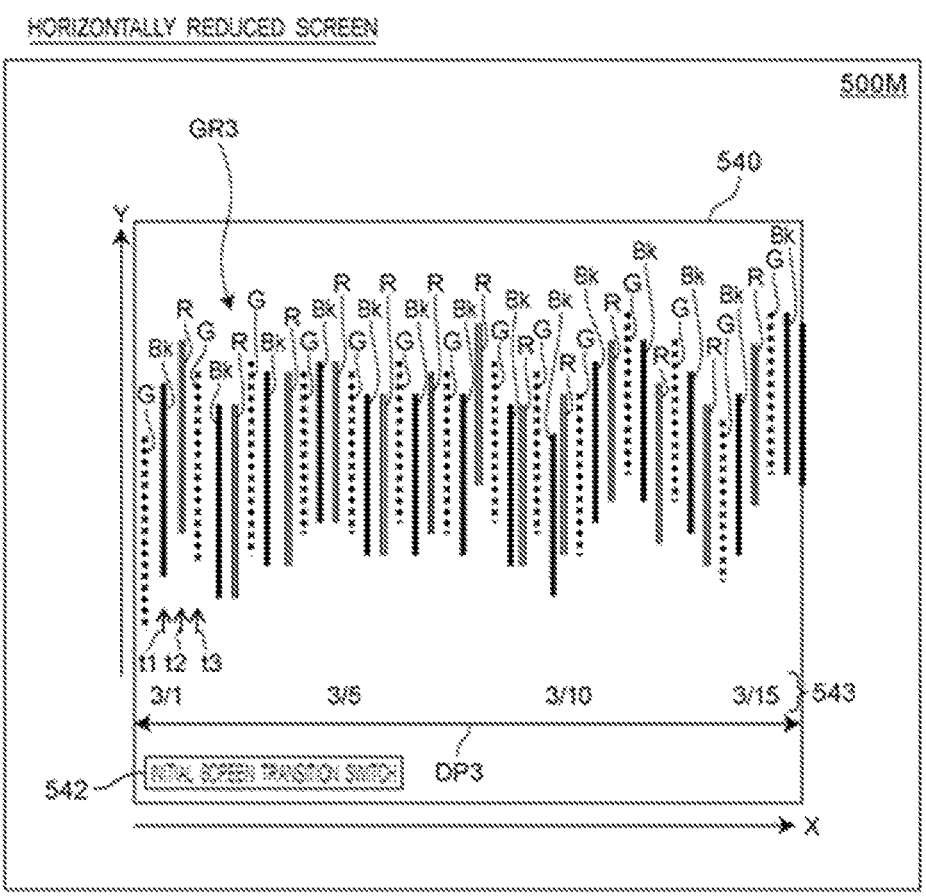
FIG. 9 is a view exemplifying a screen in a state where the initial screen is reduced in the horizontal direction.

As described later more specifically, the user can enlarge the display in the horizontal direction X as illustrated in FIG. 8 by performing operation of pinch out in the horizontal direction X on the touchpad 531. Due to this, the bar graph GR2 over a display target period DP2 from approximately March 6 to March 9 is displayed. Alternatively, the user can reduce the display in the horizontal direction X as illustrated in FIG. 9 by performing operation of pinch in in the horizontal direction X on the touchpad 531. Due to this, the bar graph GR3 over a display target period DP3 from approximately March 1 to March 15 is displayed. In FIGS. 8 and 9 (and FIGS. 10 to 23, 25, 26, 28, and 29 described later), an initial screen transition switch 542 for the user to instruct transition to the initial screen of FIG. 7 is displayed at the lowermost portion of the display unit 540 (specific usage will be described later). The display target periods DP1, DP2, and DP3 are collectively represented by a display target period DP.

Hereinafter, processing in a case where the display target period DP2 is set as illustrated in the screen of FIG. 8 and the bar graph GR2 is displayed will be described as an example.

During display of the screen of FIG. 8, in step S3 of FIG. 6A, the control unit 510 determines whether or not positions corresponding to the vertical bars Bk, R, and G at the specific times t1, t2, and t3 on the display unit 540 have been designated (touched) with the touchpad 531.

Figure 10:
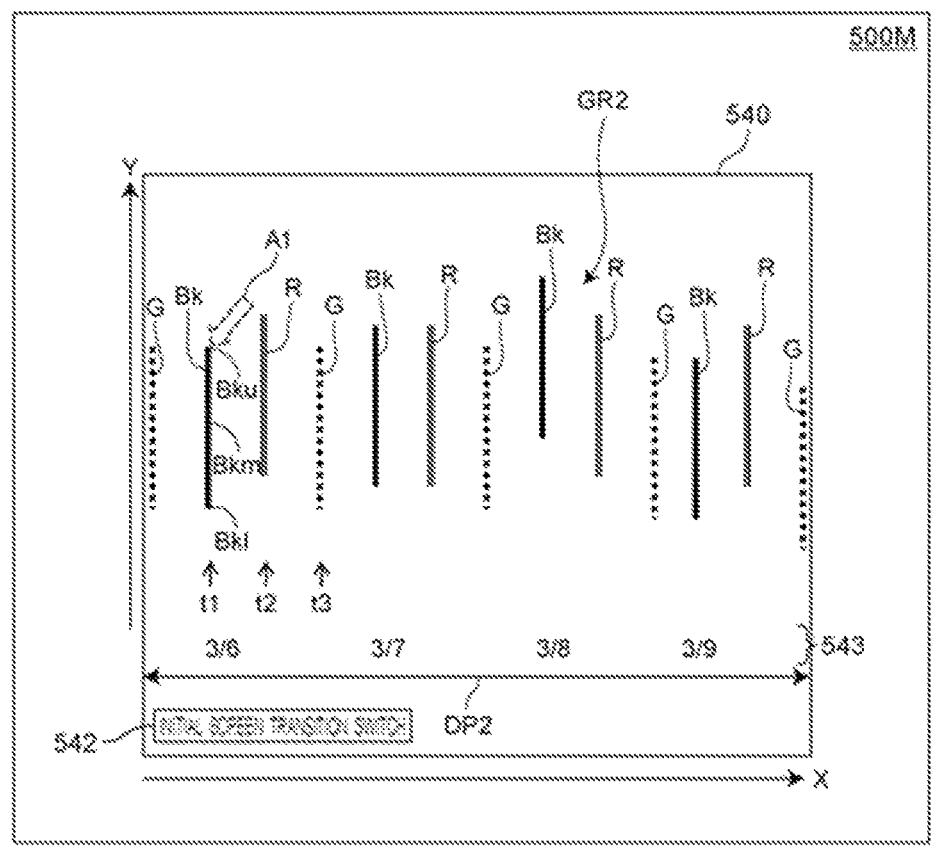
FIG. 10 is a view schematically illustrating a mode in which a position corresponding to an upper end portion of a vertical bar Bk at a specific time t1 is designated.

Here, as schematically indicated by arrow A1 in FIG. 10, it is assumed that the user operates the touchpad 531 to designate a position corresponding to an upper end portion Bku of the vertical bar Bk at the specific time t1 on the display unit 540 (Yes in step S3 in FIG. 6A).

Then, in step S4 of FIG. 6A, the control unit 510 acts as the first calculation unit, and calculates a blood pressure average value for the specific time t1 corresponding to the designated vertical bar Bk over the display target period DP2, according to the position designated. Specifically, as in the above example, when the position corresponding to the upper end portion Bku of the vertical bar Bk (indicated by arrow A1 in FIG. 10) is designated, the systolic blood pressure average value (represented by reference sign "SBPave") for the specific time t1 is obtained. When a position corresponding to a lower end portion Bk1 of the vertical bar Bk is designated, the diastolic blood pressure average value (represented by reference sign "DBPave") for the specific time t1 is obtained. When a position corresponding to a central portion Bkm of the vertical bar Bk is designated, the systolic blood pressure average value SBPave and the diastolic blood pressure average value DBPave for the specific time t1 are obtained. At this time, the control unit 510 may calculate a standard deviation value together with each blood pressure average value.

Here, assuming that the display target period DP2 is n days (n is a natural number) and the systolic blood pressure average value at the specific time t1 is SBP1, SBP2, . . . , and SBPn, the systolic blood pressure average value SBPave is defined by (SBP1+SBP2+ . . . +SBPn)/n (in the present embodiment, this definition is extended to the case of n=1). Similarly, assuming that the display target period is n days (n is a natural number) and the diastolic blood pressure average value at the specific time t1 is DBP1, DBP2, . . . , and DBPn, the diastolic blood pressure average value DBPave is defined by (DBP1+DBP2+ . . . +DBPn)/n (in the present embodiment, this definition is extended to the case of n=1).

In this example, in order to facilitate position designation, the "upper end portions" and the "lower end portions" of the vertical bars Bk, R, and G are not limited to the upper end and the lower end (end points), respectively, and include a certain range (for example, a range of about 10% of the entire lengths of the vertical bars Bk, R, and G) from the upper end and the lower end, respectively. The "central portions" of the vertical bars Bk, R, and G refer to portions other than the "upper end portions" and the "lower end portions" of the entire lengths of the vertical bars Bk, R, and G.

Figure 11:
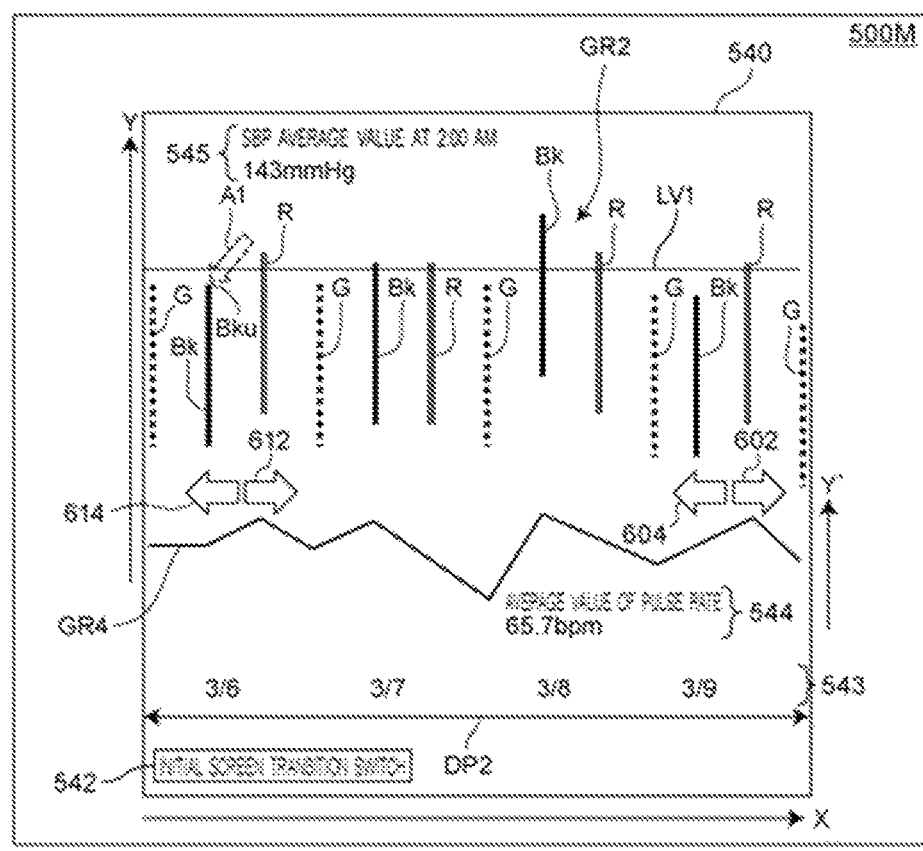
FIG. 11 is a view exemplifying content displayed on the display unit by the operation illustrated in FIG. 10.

Next, in step S5 of FIG. 6A, the control unit 510 acts as the first display control unit, and displays, on the display unit 540, the systolic blood pressure average value SBPave and/or the diastolic blood pressure average value DBPave obtained for the specific time t1 together with the bar graph GR2. As in the above example, when the systolic blood pressure average value SBPave is obtained, as exemplified in FIG. 11, the control unit 510 displays, for example, pop-up displays, on the display unit 540, the systolic blood pressure average value SBPave for the specific time t1 together with the bar graph GR2. In the example of FIG. 11, in an area 545 separated upward from the bar graph GR2 on the display unit 540, the systolic blood pressure average value SBPave is displayed as a digital value such as

"SBP AVERAGE VALUE AT 2:00 AM 143 mmHg". This allows the user to accurately know the systolic blood pressure average value SBPave. This pop-up display continues for a predetermined period, for example, 5 seconds, and then automatically disappears. The pop-up display does not automatically disappear if a predetermined position, for example, any position of the pop-up display portion is touched during the display, and the display continues, and disappears if the same position is touched again.

Along with this, the control unit 510 acts as the first display control unit, and pop-up displays, on the display unit 540, the systolic blood pressure average value SBPave as a horizontal bar LV1 superimposed on the bar graph GR2. This allows the user to intuitively grasp the position of the systolic blood pressure average value SBPave with respect to the bar graph GR2.

The control unit 510 acts as the first display control unit, and pop-up displays, on the display unit 540, a change in the pulse rate over the display target period DP2 as a line graph GR4 along the lower side of the bar graph GR2 in this example (Y' represents a coordinate axis regarding the pulse rate). Along with this, in this example, in an area 544 along the lower side of the line graph GR4, an average value of the pulse rate over the display target period DP2 is pop-up displayed as a digital value such as

"AVERAGE VALUE OF PULSE RATE 65.7 bpm". Here, the pulse rate indicates a rest level (a level whether to be in a resting state or to be in a moving state) of the subject at the time of blood pressure measurement. With these displays, the user can intuitively judge whether or not a change in a blood pressure value over the display target period DP2 indicated by the bar graph GR2 is due to the rest level of the subject.

However, the horizontal bar LV1 indicating the systolic blood pressure average value SBPave and the line graph GR4 indicating the change in the pulse rate are not essential display content and correspond to additional display content. For example, when the user operates the touchpad 531 on the screen of FIG. 10, the horizontal bar LV1 and the line graph GR4 may be pop-up displayed on a condition that the position corresponding to the upper end portion Bku of the vertical bar Bk at the specific time t1 on the display unit 540 is long pressed (described later) instead of the normal position designation (short press). This allows the user to increase the amount of information to be displayed by operation along his/her natural sense.

When a position corresponding to the lower end portion Bk1 (see FIG. 10) of the vertical bar Bk at the specific time t1 is designated in step S3 of FIG. 6A, the diastolic blood pressure average value DBPave for the specific time t1 is calculated in step S4 of FIG. 6A. Then, in step S5 of FIG. 6A, the obtained diastolic blood pressure average value DBPave is pop-up displayed as a digital value in an area separated downward from the bar graph GR2 in the display unit 540 together with the bar graph GR2. Along with this, the diastolic blood pressure average value DBPave is graphically displayed as a horizontal bar (not illustrated) superimposed on the bar graph GR2.

When a position corresponding to the central portion Bkm (see FIG. 10) of the vertical bar Bk at the specific time t1 is designated in step S3 of FIG. 6A, the systolic blood pressure average value SBPave and the diastolic blood pressure average value DBPave for the specific time t1 are calculated in step S4 of FIG. 6A. Then, in step S5 of FIG. 6A, together with the bar graph GR2, the obtained systolic blood pressure average value SBPave and the diastolic blood pressure average value DBPave are pop-up displayed as digital values in areas separated upward and downward from the bar graph GR2 in the display unit 540. Along with this, the systolic blood pressure average value SBPave and the diastolic blood pressure average value DBPave are graphically displayed as horizontal bars (not illustrated) superimposed on the bar graph GR2.

Thus, according to the system 100 (in particular, the personal terminal 500), the blood pressure average value (the systolic blood pressure average value SBPave and/or the diastolic blood pressure average value DBPave) over a plurality of days (the display target period DP2) for the specific time t1 can be displayed on the display unit 540 with simple operation (that is, single touch operation by the user designating a position corresponding to the vertical bar Bk at the specific time t1 on the display unit 540 using the touchpad 531). Here, the upper end portion Bku of the vertical bar Bk represents SBP, and the lower end portion Bk1 represents DBP. Therefore, when the user designates a portion of the vertical bar Bk (the upper end portion Bku, the lower end portion Bk1, or the central portion Bkm illustrated in FIG. 10) representing the blood pressure value corresponding to the blood pressure average value that he/she desires to display, the blood pressure average value (the systolic blood pressure average value SBPave, the diastolic blood pressure average value DBPave, or both the systolic blood pressure average value SBPave and the diastolic blood pressure average value DBPave) that he/she desires to display can be pop-up displayed. That is, the user can pop-up display the blood pressure average value that he/she desires to display by operation along his/her natural sense.

In the above example, the case of displaying the blood pressure average value over the display target period DP2 for the time t1 among the times t1, t2, and t3 at which the blood pressure is measured has been described, but the present invention is not limited to this. Similarly, for the time t2 or t3, the blood pressure average value over a plurality of days (the display target period DP2) for the specific time t2 or t3 can be pop-up displayed on the display unit 540 with simple operation (that is, single touch operation by the user designating positions corresponding to the vertical bars R or G at the specific time on the display unit 540 using the touchpad 531).

(Modification 1; Case where the Upper End Portion and the Lower End Portion of the Vertical Bar are Consecutively Designated)

Figure 12:
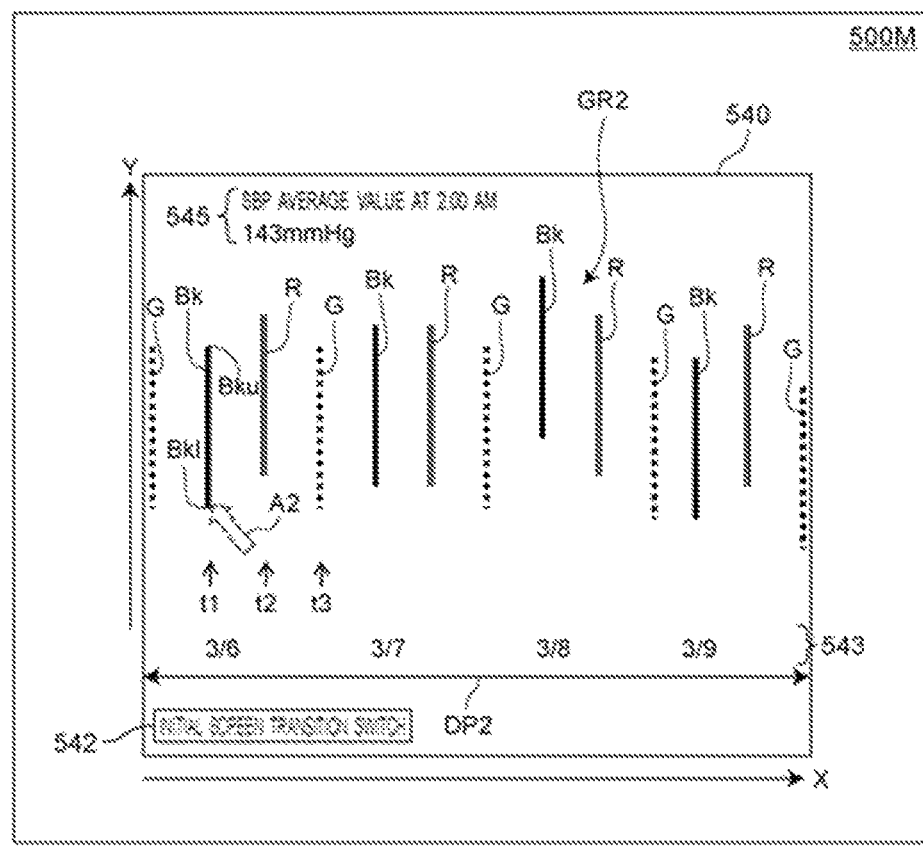
FIG. 12 is a view schematically illustrating a mode in which after the position corresponding to the upper end portion of the vertical bar Bk at the specific time t1 is designated, a position corresponding to a lower end portion of the vertical bar Bk is consecutively designated.

FIG. 12 schematically illustrates a mode in which the position corresponding to the upper end portion Bku of the vertical bar Bk at the specific time t1 is designated as described above, and then the position corresponding to the lower end portion Bk1 of the vertical bar Bk is consecutively designated on the screen of FIG. 10.

Specifically, the user operates the touchpad 531 to designate the position corresponding to the upper end portion Bku of the vertical bar Bk at the specific time t1, and then consecutively designates the position corresponding to the lower end portion Bk1 of the vertical bar Bk as schematically indicated by arrow A2 in FIG. 12. "Consecutively designate" refers to designation regarded as designation substantially related to previous designation, such as designation within the predetermined period (5 seconds) or within one second, for example.

Figure 13:
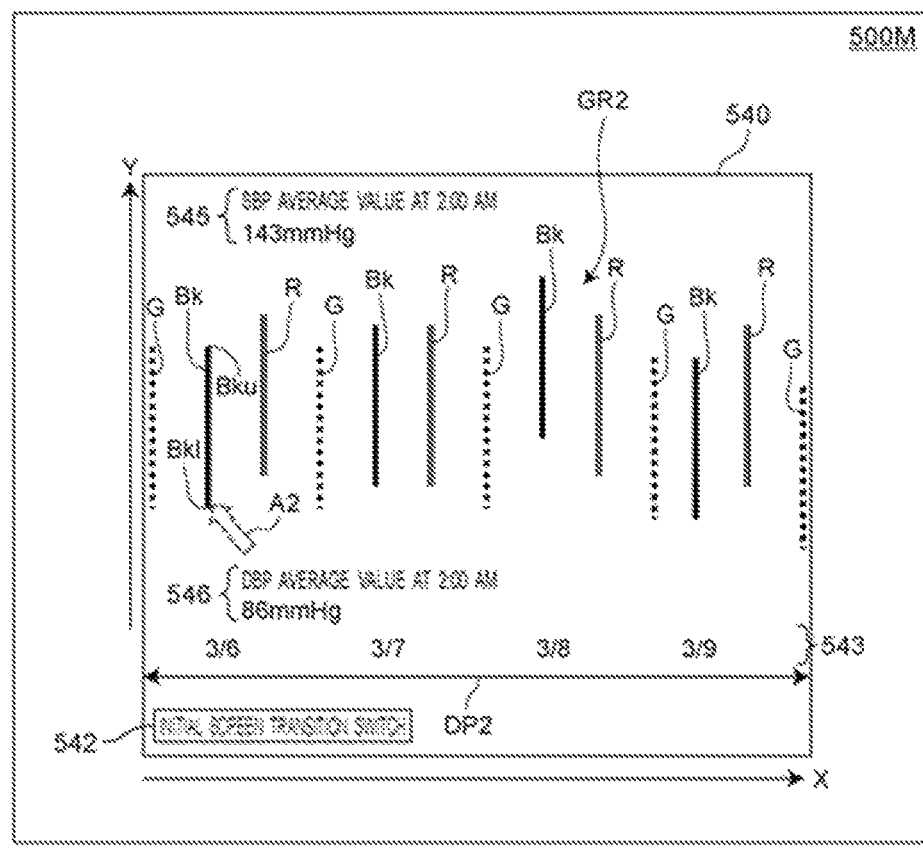
FIG. 13 is a view exemplifying content displayed on the display unit by the operation illustrated in FIG. 12.

Then, the control unit 510 acts as the first display control unit, and displays, on the display unit 540, the diastolic blood pressure average value DBPave corresponding to the lower end portion Bk1 for the specific time t1 in addition to the systolic blood pressure average value SBPave corresponding to the upper end portion Bku for the specific time t1 as exemplified in FIG. 13. In the example of FIG. 13, in an area 546 separated downward from the bar graph GR2 on the display unit 540, the diastolic blood pressure average value DBPave is pop-up displayed as a digital value such as

"DBP AVERAGE VALUE AT 2:00 AM 86 mmHg". This allows the user to accurately know the systolic blood pressure average value SBPave and the diastolic blood pressure average value DBPave.

On the contrary, when the position corresponding to the lower end portion Bk1 of the vertical bar Bk at the specific time t1 is designated first and then the position corresponding to the upper end portion Bku of the vertical bar Bk is consecutively designated, the systolic blood pressure average value SBPave corresponding to the upper end portion Bku for the specific time t1 is pop-up displayed in addition to the diastolic blood pressure average value DBPave corresponding to the lower end portion Bk1 for the specific time t1.

Thus, in Modification 1, after the position corresponding to the end portion of any one of the upper end portion Bku and the lower end portion Bk1 of the vertical bar Bk at the specific time 11 on the display unit 540 is designated with the touchpad 531, when the position corresponding to the other end portion of the vertical bar Bk is consecutively designated with the touchpad 531, the control unit 510 acts as the first display control unit and pop-up displays, on the display unit 540, the blood pressure average value corresponding to the other end portion for the specific time t1 in addition to the blood pressure average value corresponding to the one end portion for the specific time t1. Therefore, the user can display both blood pressure average values (here, the systolic blood pressure average value SBPave and the diastolic blood pressure average value DBPave for the specific time t1) by operation along his/her natural sense. Modification 1 can be similarly applied to the time t2 or t3.

(Modification 2; Case where the Upper End Portion of the Vertical Bar and the Upper End Portion of Another Vertical Bar are Consecutively Designated)

Figure 14:
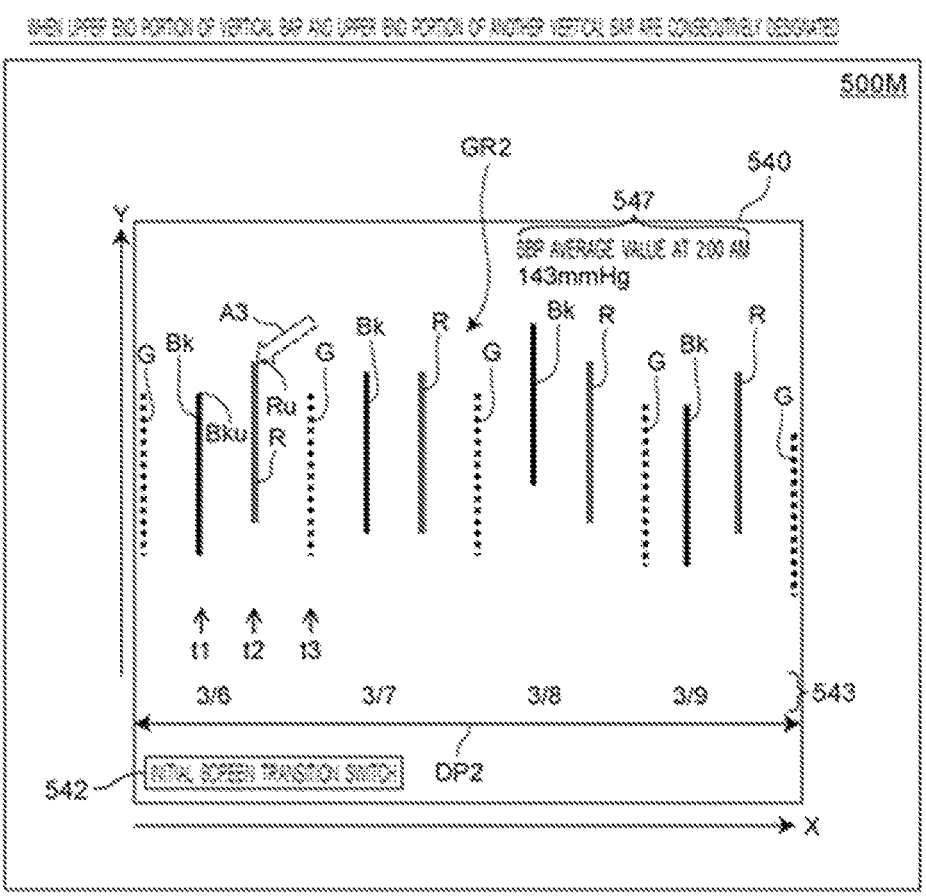
FIG. 14 is a view schematically illustrating a mode in which after the position corresponding to the upper end portion of the vertical bar Bk at the specific time (first time) t1 is designated, a position corresponding to the same upper end portion of a vertical bar R at another time (second time) t2 is consecutively designated.

FIG. 14 schematically illustrates a mode in which the position corresponding to the upper end portion Bku of the vertical bar Bk at the specific time t1 is designated as described above, and then a position corresponding to the same portion (that is, an upper end portion Ru) of the vertical bar R at another time (the time t2 in the example of FIG. 14) is consecutively designated on the screen of FIG. 10.

Specifically, the user operates the touchpad 531 to designate the position corresponding to the upper end portion Bku of the vertical bar Bk at the specific time t1, and then consecutively designates the position corresponding to the upper end portion Ru of the vertical bar R at the time 12 as schematically indicated by arrow A3 in FIG. 14.

Figure 15:
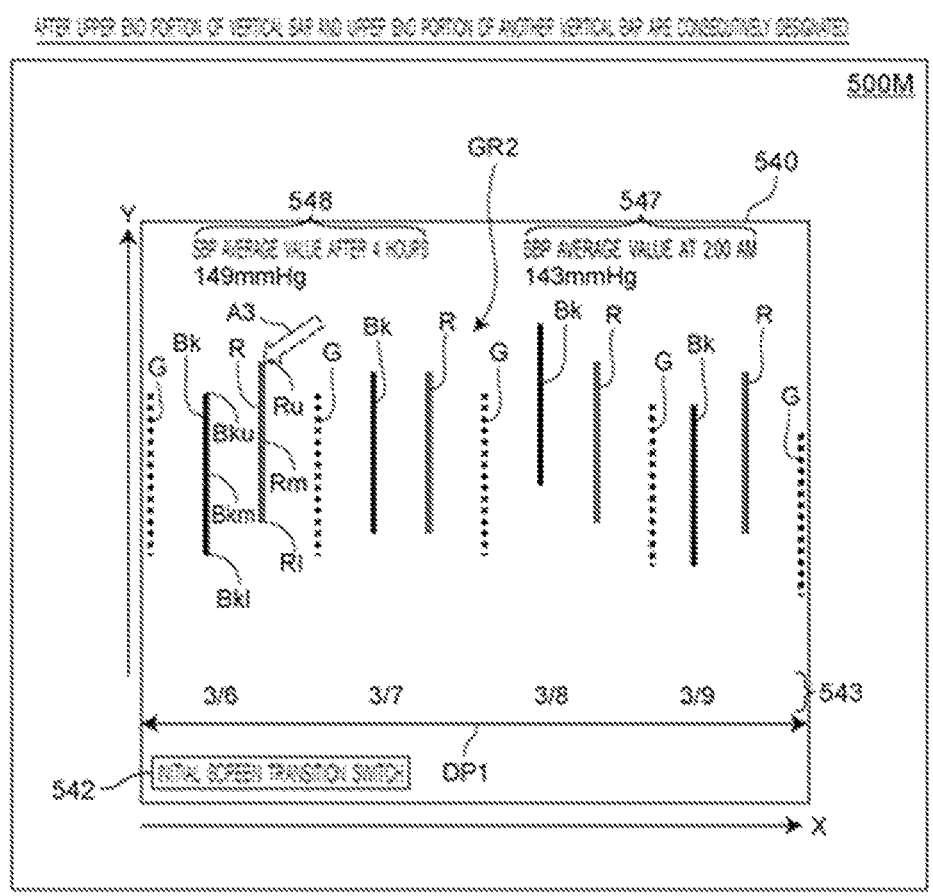
FIG. 15 is a view exemplifying content displayed on the display unit by the operation illustrated in FIG. 14.

Then, the control unit 510 acts as the first display control unit, and displays, on the display unit 540, the systolic blood pressure average value SBPave corresponding to the upper end portion Ru for the time t2 in addition to the systolic blood pressure average value SBPave (displayed in an area 547 separated right upward from the bar graph GR2) corresponding to the upper end portion Bku for the specific time t1 as exemplified in FIG. 15. In the example of FIG. 15, in an area 547 separated right upward from the bar graph GR2 on the display unit 540, the systolic blood pressure average value SBPave for the time t1 is displayed as a digital value such as "SBP AVERAGE VALUE AT 2:00 AM
143 mmHg". In addition, in an area 548 separated left upward from the bar graph GR2 on the display unit 540, the systolic blood pressure average value SBPave for the time t2 is displayed as a digital value such as
"SBP AVERAGE VALUE AFTER 4 HOURS
149 mmHg". This allows the user to pop-up display the systolic blood pressure average value SBPave for both the times t1 and t2 by operation along his/her natural sense.

As known from FIG. 15, when the position corresponding to the lower end portion Bk1 of the vertical bar Bk at the specific time t1 is designated first and then the position corresponding to a lower end portion R1 of the vertical bar R at the time t2 is consecutively designated, the diastolic blood pressure average value DBPave corresponding to the lower end portion R1 for the time t2 is pop-up displayed on the display unit 540 in addition to the diastolic blood pressure average value DBPave corresponding to the lower end portion Bk1 for the specific time t1. When the position corresponding to the central portion Bkm of the vertical bar Bk at the specific time t1 is designated first and then the position corresponding to a central portion Rm of the vertical bar R at the time t2 is consecutively designated, the systolic blood pressure average value SBPave and the diastolic blood pressure average value DBPave corresponding to the lower end portion R1 for the time 12 are pop-up displayed on the display unit 540 in addition to the systolic blood pressure average value SBPave and the diastolic blood pressure average value DBPave corresponding to the central portion Bkm for the specific time t1.

Figure 16:
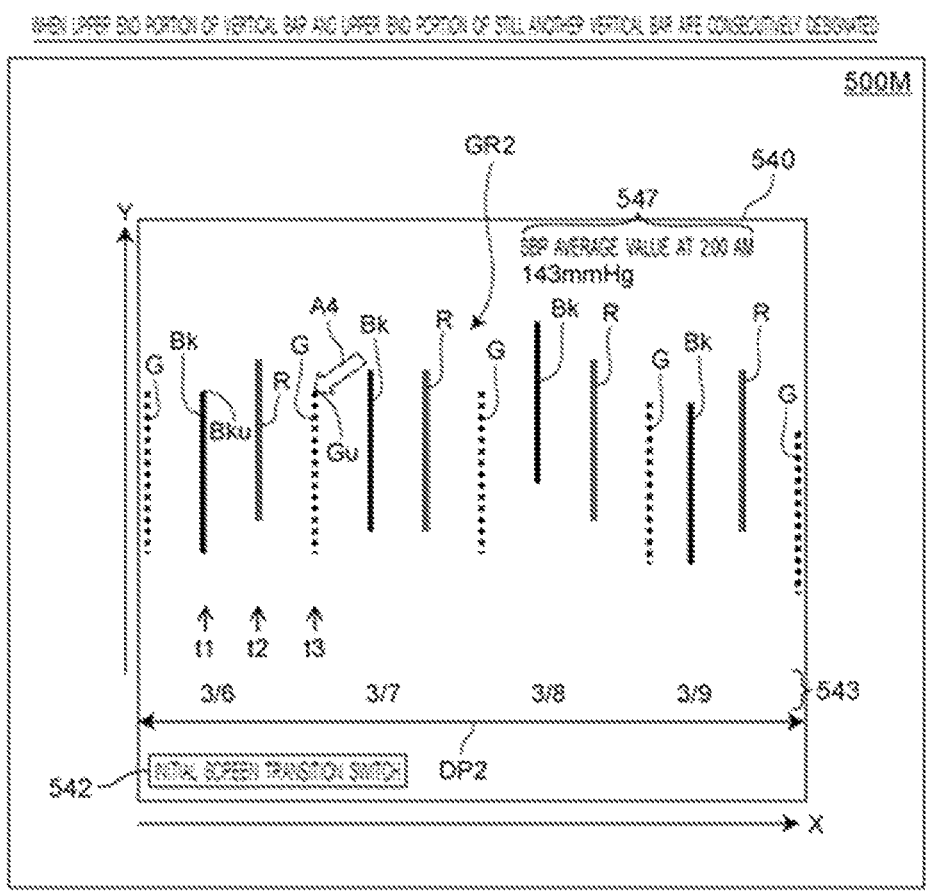
FIG. 16 is a view schematically illustrating a mode in which after the position corresponding to the upper end portion of the vertical bar Bk at the specific time (first time) t1 is designated, a position corresponding to the same upper end portion of a vertical bar G at still another time (third time) t3 is consecutively designated.

FIG. 16 schematically illustrates a mode in which the position corresponding to the upper end portion Bku of the vertical bar Bk at the specific time t1 is designated as described above, and then a position corresponding to the same portion (that is, an upper end portion Gu) of the vertical bar G at still another time (the time t3 in the example of FIG. 16) is consecutively designated on the screen of FIG. 10.

Specifically, the user operates the touchpad 531 to designate the position corresponding to the upper end portion Bku of the vertical bar Bk at the specific time t1, and then consecutively designates the position corresponding to the upper end portion Gu of the vertical bar G at the time t3 as schematically indicated by arrow A4 in FIG. 16.

Figure 17:
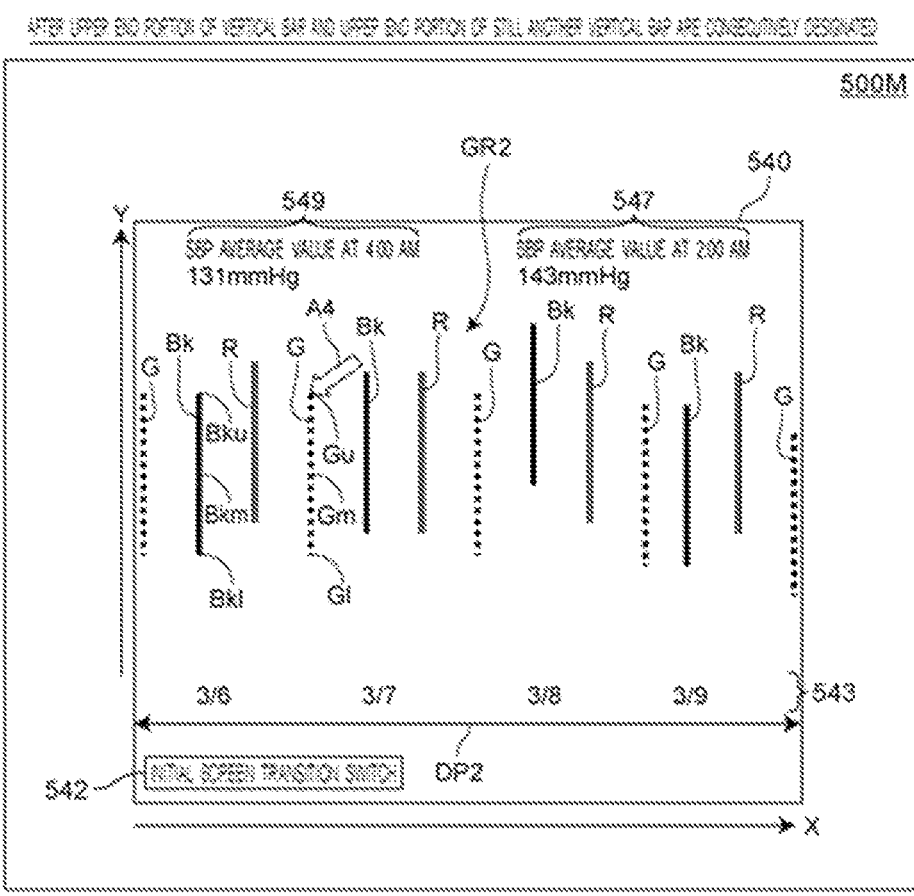
FIG. 17 is a view exemplifying content displayed on the display unit by the operation illustrated in FIG. 16.

Then, the control unit 510 acts as the first display control unit, and pop-up displays, on the display unit 540, the systolic blood pressure average value SBPave corresponding to the upper end portion Gu for the time t3 in addition to the systolic blood pressure average value SBPave (displayed in the area 547 separated right upward from the bar graph GR2) corresponding to the upper end portion Bku for the specific time t1 as exemplified in FIG. 17. In the example of FIG. 17, in an area 547 separated right upward from the bar graph GR2 on the display unit 540, the systolic blood pressure average value SBPave is pop-up displayed as a digital value such as "SBP AVERAGE VALUE AT 2:00 AM
143 mmHg". In addition, in an area 549 separated left upward from the bar graph GR2 on the display unit 540, the systolic blood pressure average value SBPave is pop-up displayed as a digital value such as
"SBP AVERAGE VALUE AT 4:00 AM
149 mmHg". This allows the user to pop-up display the systolic blood pressure average value SBPave for both the times t1 and t3 by operation along his/her natural sense.

As known from FIG. 17, when the position corresponding to the lower end portion Bk1 of the vertical bar Bk at the specific time t1 is designated first and then the position corresponding to a lower end portion G1 of the vertical bar G at the time t3 is consecutively designated, the diastolic blood pressure average value DBPave corresponding to the lower end portion G1 for the time t3 is pop-up displayed on the display unit 540 in addition to the diastolic blood pressure average value DBPave corresponding to the lower end portion Bk1 for the specific time t1. When the position corresponding to the central portion Bkm of the vertical bar Bk at the specific time t1 is designated first and then the position corresponding to a central portion Gm of the vertical bar G at the time t3 is consecutively designated, the systolic blood pressure average value SBPave and the diastolic blood pressure average value DBPave corresponding to the central portion Gm for the time t3 are pop-up displayed on the display unit 540 in addition to the systolic blood pressure average value SBPave and the diastolic blood pressure average value DBPave corresponding to the central portion Bkm for the specific time t1.

Modification 2 can be similarly applied not only to the case where the designation order is from the time t1 to the time t2 or t3 but also to the case where the designation order is from the time t2 to the time t3 or t1 and the case where the designation order is from the time t3 to the time t1 or t2.

Returning to FIG. 6A, it is assumed that, on the display unit 540, positions corresponding to the vertical bars Bk, R, and G of the bar graph GR2 are not designated (No in step S3) but an area separated upward or downward from the bar graph GR2 is designated (Yes in step S6).

Figure 18:
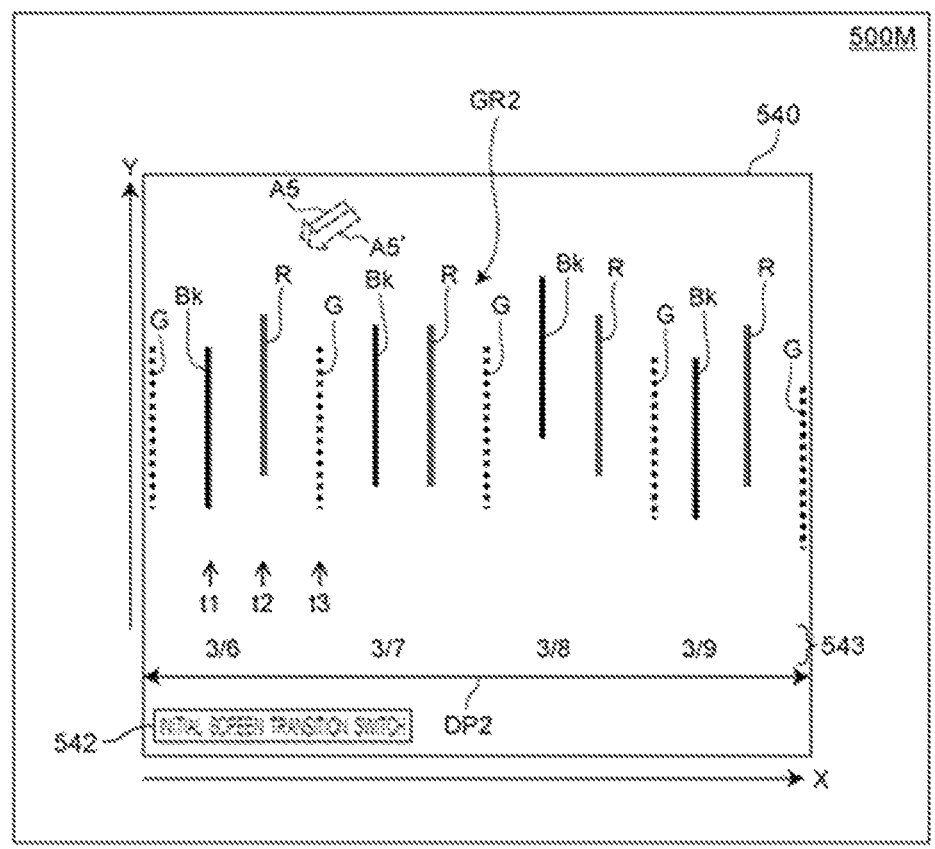
FIG. 18 is a view schematically illustrating a mode in which a position separated upward from a bar graph is designated.

For example, FIG. 18 schematically illustrates a mode in which a position separated upward from the bar graph GR2 is designated in step S6 of FIG. 6A. Specifically, it is assumed that the user operates the touchpad 531 to consecutively designate (double tap) two times a position corresponding to an area separated upward from the bar graph GR2 as schematically illustrated by double arrows A5 and A5' in FIG. 18.

Then, in step S7 of FIG. 6A, the control unit 510 acts as the second calculation unit, and averages data of SBP stored in the memory 520 over the display target period DP2 with putting together the plurality of times t1, t2, and t3 to obtain a systolic blood pressure average value (this is represented by reference sign "SBPave'") for the plurality of times t1, t2, and t3 being put together.

Figure 19:
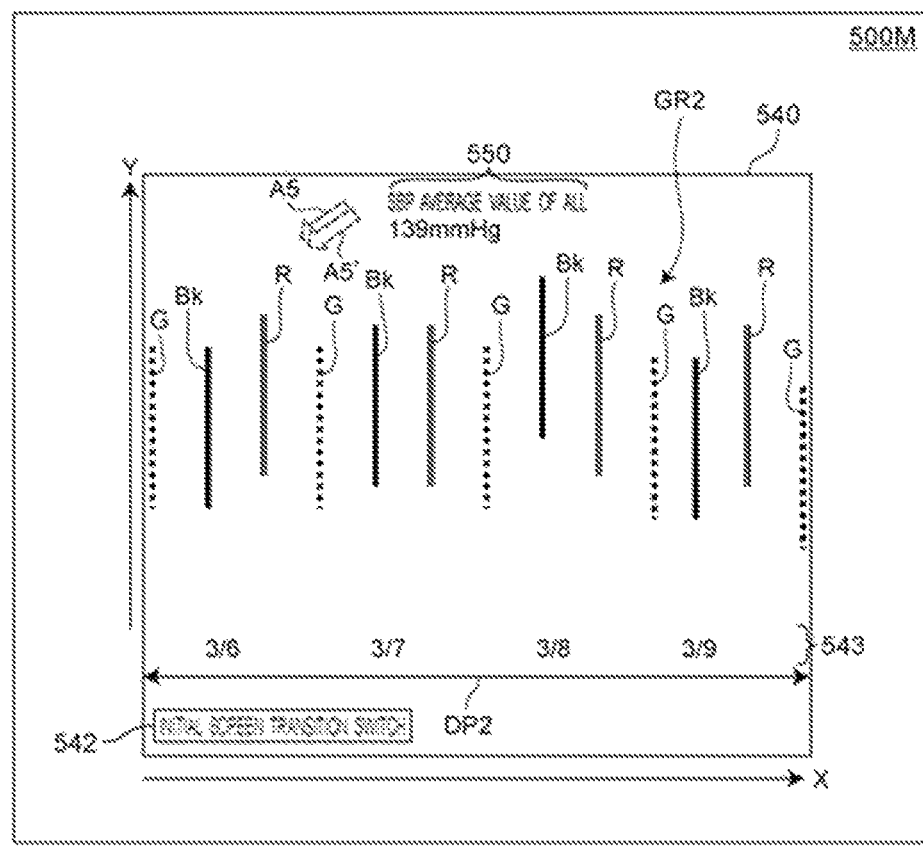
FIG. 19 is a view exemplifying content displayed on the display unit by the operation illustrated in FIG. 18.

Subsequently, in step S8 of FIG. 6A, the control unit 510 acts as the second display control unit, and pop-up displays the systolic blood pressure average value SBPave' obtained with putting together the plurality of times t1, t2, and t3 together with the bar graph GR2 on the display unit 540 as exemplified in FIG. 19. In the example of FIG. 19, in an area 550 away upward from the bar graph GR2 in the display unit 540, the systolic blood pressure average value SBPave' obtained with putting together the plurality of times t1, t2, and t3 is pop-up displayed as a digital value such as

"SBP AVERAGE VALUE OF ALL 139 mmHg".

Figure 20:
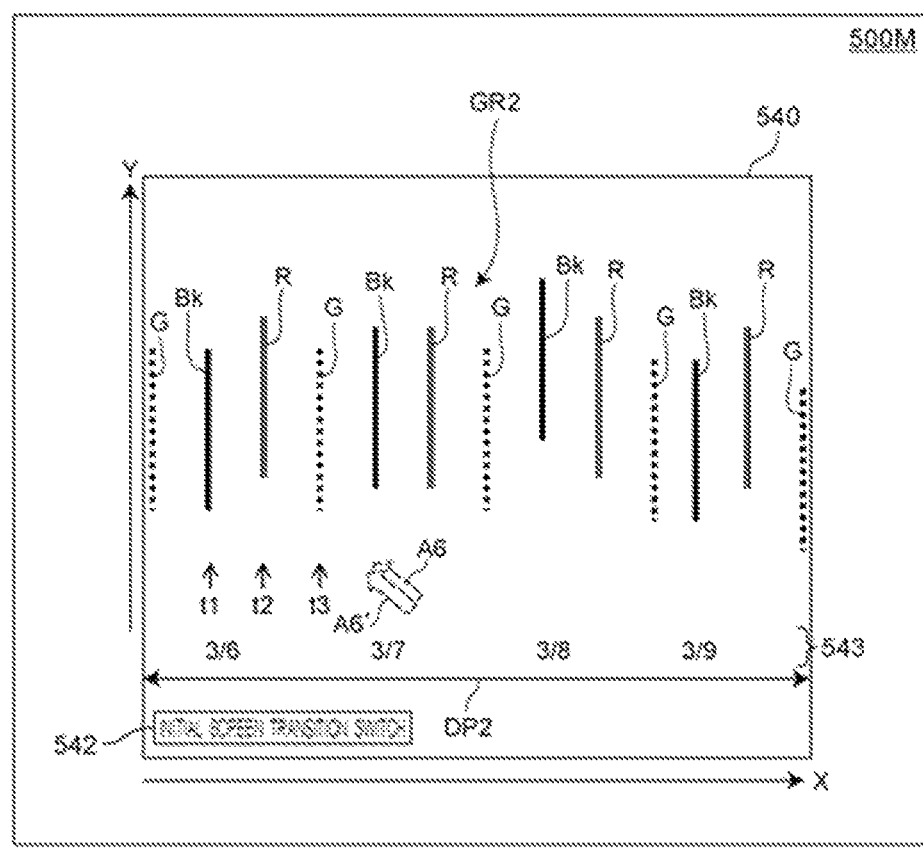
FIG. 20 is a view schematically illustrating a mode in which a position separated downward from a bar graph is designated.

On the other hand, FIG. 20 schematically illustrates a mode in which a position separated downward from the bar graph GR2 is designated in step S6 of FIG. 6A. Specifically, it is assumed that the user operates the touchpad 531 to consecutively designate (double tap) two times a position corresponding to an area separated downward from the bar graph GR2 as schematically illustrated by double arrows A6 and A6' in FIG. 20.

Then, in step S7 of FIG. 6A, the control unit 510 acts as the second calculation unit, and averages data of DBP stored in the memory 520 over the display target period DP2 with putting together the plurality of times t1, t2, and t3 to obtain a diastolic blood pressure average value (this is represented by reference sign "DBPave'") for the plurality of times t1, t2, and t3 being put together.

Figure 21:
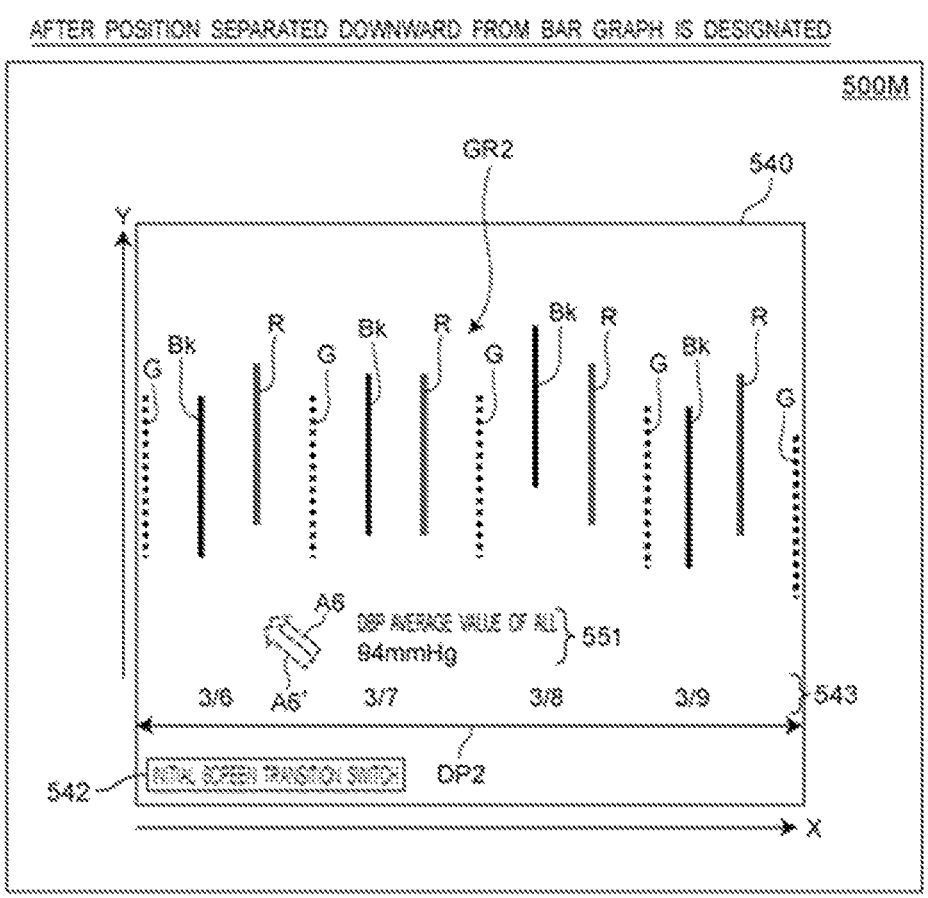
FIG. 21 is a view exemplifying content displayed on the display unit by the operation illustrated in FIG. 20.

Subsequently, in step S8 of FIG. 6A, the control unit 510 acts as the second display control unit, and pop-up displays the diastolic blood pressure average value DBPave' obtained with putting together the plurality of times t1, t2, and t3 together with the bar graph GR2 on the display unit 540 as exemplified in FIG. 21. In the example of FIG. 21, in an area 551 away downward from the bar graph GR2 in the display unit 540, the diastolic blood pressure average value DBPave' obtained with putting together the plurality of times t1, t2, and t3 is pop-up displayed as a digital value such as

"DBP AVERAGE VALUE OF ALL 94 mmHg".

Thus, according to the system 100 (in particular, the personal terminal 500), the blood pressure average value over the display target period DP2 with putting together the specific times t1, t2, and t3 can be pop-up displayed on the display unit 540 with simple operation (that is, operation by the user designating the area 550 separated upward or the area 551 separated downward from the bar graph GR2 on the display unit 540 using the touchpad 531).

Next, in step S9 of FIG. 6B, the control unit 510 determines whether or not operation of pinch out, pinch in, and/or slide has been performed in the horizontal direction X by the touchpad 531 on the display unit 540. Here, when operation of pinch out or pinch in is performed in the horizontal direction X on the touchpad 531 (Yes in step S9 of FIG. 6B), the control unit 510 acts as the initial display control unit, and changes the display target period by enlarging or reducing the display in the horizontal direction X on the display unit 540 (step S10 of FIG. 6B). In place of this or together with this, when operation of sliding in the horizontal direction X on the touchpad 531 is performed (Yes in step S9 of FIG. 6B), the control unit 510 shifts the display target period (step S10 of FIG. 6B). Thereafter, returning to step S2 of FIG. 6A, the control unit 510 acts as the initial display control unit, and displays, on the display unit 540, a screen corresponding to the display target period after change. Therefore, the user can change the display target period in real time with simple operation (that is, operation of pinch out or pinch in and/or operation of slide) as exemplified in FIGS. 7 to 9. When operation of pinch in or pinch out is performed during the period in which pop-up display is performed, the display target period DP2 is changed (shortened or extended), and information over the changed period, for example, an average value is immediately calculated. The calculated result is immediately reflected in the pop-up display, and the average value indicated in the pop-up display is instantaneously updated.

When operation of pinch out or pinch in and/or slide as described above is not performed in step S9 of FIG. 6B (No in step S9 of FIG. 6B), the control unit 510 determines whether or not the initial screen transition switch 542 is turned on with the touchpad 531 on the display unit 540 (step S11 of FIG. 6B). Here, when the initial screen transition switch 542 is turned on with the touchpad 531 on the display unit 540, the control unit 510 acts as the initial display control unit and returns the display target period to a default period, that is, the display target period DP1 illustrated in FIG. 7 (step S12 in FIG. 6B). Thereafter, returning to step S2 of FIG. 6A, the control unit 510 acts as the initial display control unit, and displays, on the display unit 540, the initial screen of FIG. 7 again.

When there is no operation in step S11 of FIG. 6B (No in step S11), the control unit 510 returns to step S9 and waits for some operation.

(Modification 3; Case where the Amount of Information to be Displayed Increases by Long Press)

In Modification 3, when a specific position on the display unit 540 is long pressed with the touchpad 531 in step S3 of FIG. 6A, the control unit 510 acts as the first display control unit, and increases the amount of information displayed together with the bar graph GR2 on the display unit 540 as compared with the amount of information displayed with normal position designation (short press). Note that "long press" means that designation (press) with the touchpad 531 is continuously continued for a certain period of time (for example, 3 seconds) or more.

Figure 22:
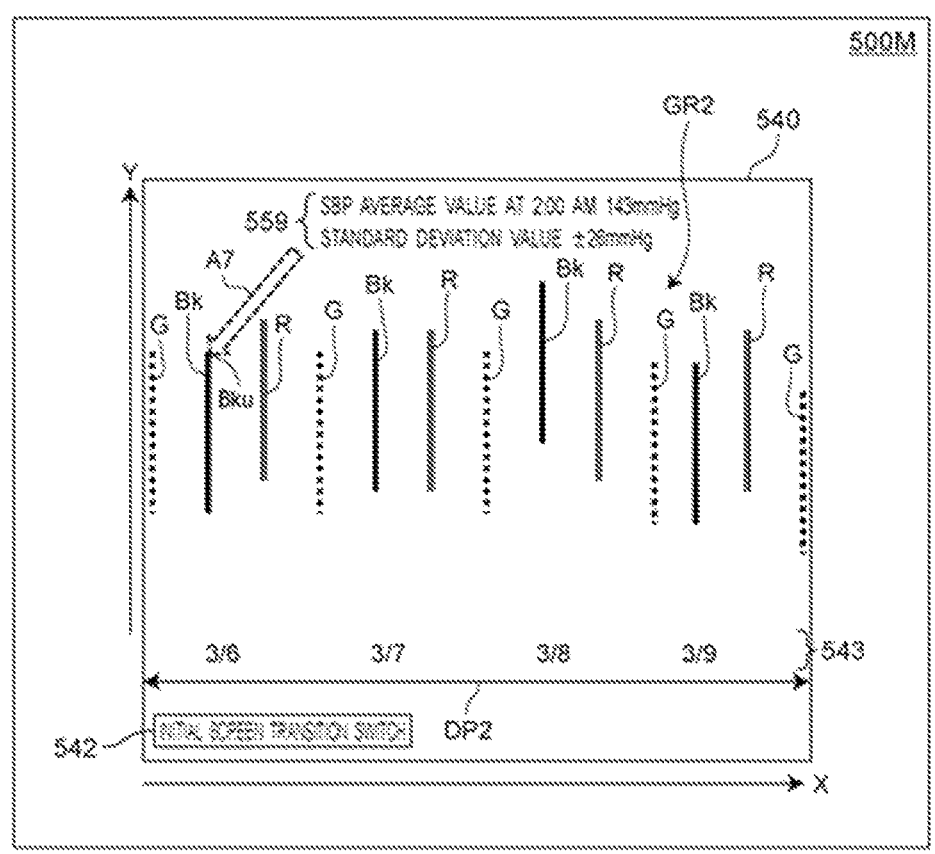
FIG. 22 is a view schematically illustrating a mode in which a position corresponding to the upper end portion of the vertical bar Bk at the specific time (first time) t1 is long pressed.

As an example, it is assumed that, when the user operates the touchpad 531 on the screen of FIG. 10, the position corresponding to the upper end portion Bku of the vertical bar Bk at the specific time t1 on the display unit 540 is long pressed as schematically indicated by long arrow A7 in FIG. 22 instead of short press. Then, the control unit 510 acts as the first display control unit, and in this example, pop-up displays the standard deviation value together with the systolic blood pressure average value SBPave in an area 559 along the upper side in the display unit 540. In the example of FIG. 22, the systolic blood pressure average value SBPave and the standard deviation value are pop-up displayed as digital values such as "SBP AVERAGE VALUE AT 2:00 AM 143 mmHg STANDARD DEVIATION VALUE±26 mmHg".

Figure 23:
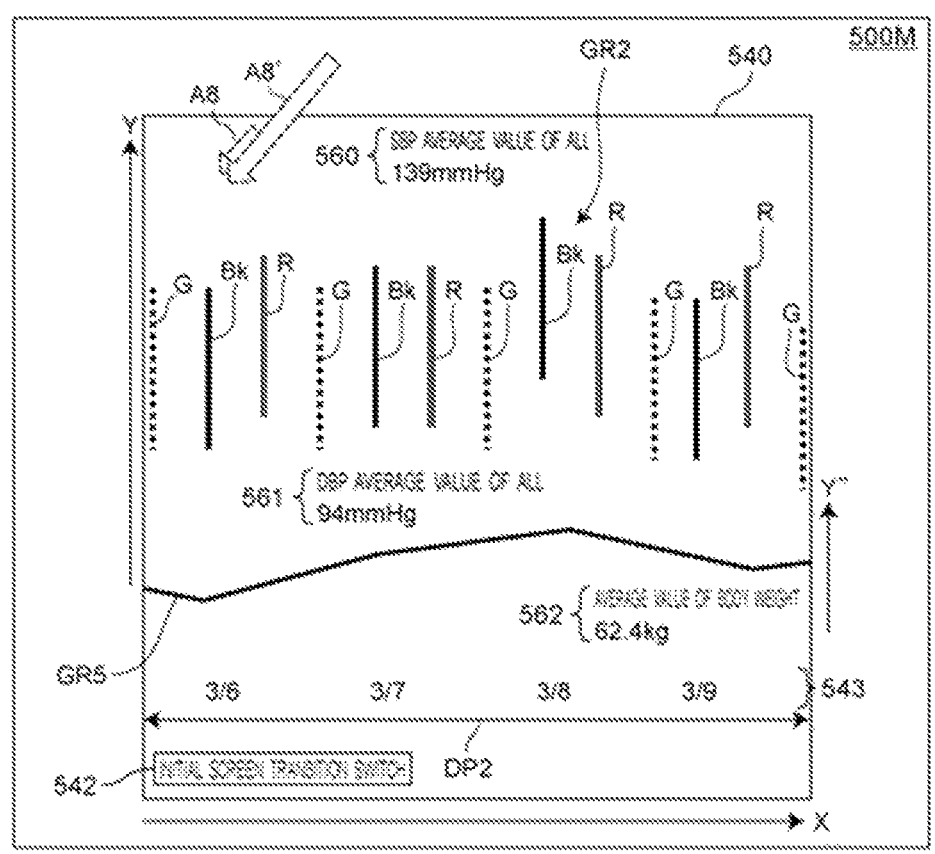
FIG. 23 is a view schematically illustrating a mode in which a position corresponding to an area separated upward from a bar graph GR2 in a display unit 540 is short pressed once and is continuously long pressed once.

As another example, it is assumed that when operating the touchpad 531 on the screen of FIG. 18, the user short presses once and consecutively long presses once, as schematically indicated by short arrow A8 and long arrow A8' in FIG. 23, a position corresponding to an area separated upward from the bar graph GR2 in the display unit 540, instead of short press (double tap) twice in a row. Then, the control unit 510 acts as the first display control unit, and in this example, pop-up displays the systolic blood pressure average value SBPave' and the diastolic blood pressure average value DBPave' with putting together the plurality of times t1, t2, and t3 in respective areas 560 and 561 separated upward and downward from the bar graph GR2 in the display unit 540. In the example of FIG. 23, in areas 560 and 561 along the upper side and the lower side in the display unit 540, the systolic blood pressure average value SBPave' and the diastolic blood pressure average value DBPave' are respectively pop-up displayed as digital values such as

"SBP AVERAGE VALUE OF ALL 139 mmHg",

"DBP AVERAGE VALUE OF ALL 94 mmHg". In the example of FIG. 23, a change in the body weight of the subject over the display target period DP2 is pop-up displayed as a line graph GR5 along the lower side of the bar graph GR2 in the display unit 540 (Y" represents a coordinate axis regarding the body weight). Furthermore, in an area 562 along the lower side of the line graph GR5, the average value of the body weight of the subject over the display target period DP2 is pop-up displayed as a digital value such as

"AVERAGE VALUE OF BODY WEIGHT 62.4 kg". It is assumed that data of the body weight of the subject is stored in the memory 520 in advance by being received together with the blood-pressure-related data in step S1 of FIG. 6A, being manually input via the operation unit 530, or being input by voice recognition using the speech analysis/recognition unit 580.

In this manner, by long-pressing the touchpad 531, the user can increase the amount of information to be displayed. Therefore, the user can increase the amount of information to be displayed with operation according to his/her natural sense.

Modification 3 can be similarly applied even if the area subjected to one short press and consecutive one long press is an area separated downward from the bar graph GR2 (however, upper than the date display area 543) in the display unit 540.

(Modification 4; Case where Blood Pressure Average Values in the First Half and the Second Half of a Display Target Period are Displayed by Long Press)

In Modification 4, as another mode in which the amount of information to be displayed is increased when a position corresponding to the vertical bar at a specific time on the display unit 540 is long pressed with the touchpad 531, an example will be described, in which the blood pressure average values in the first half and the second half of the display target period DP2 are displayed.

Figure 24:
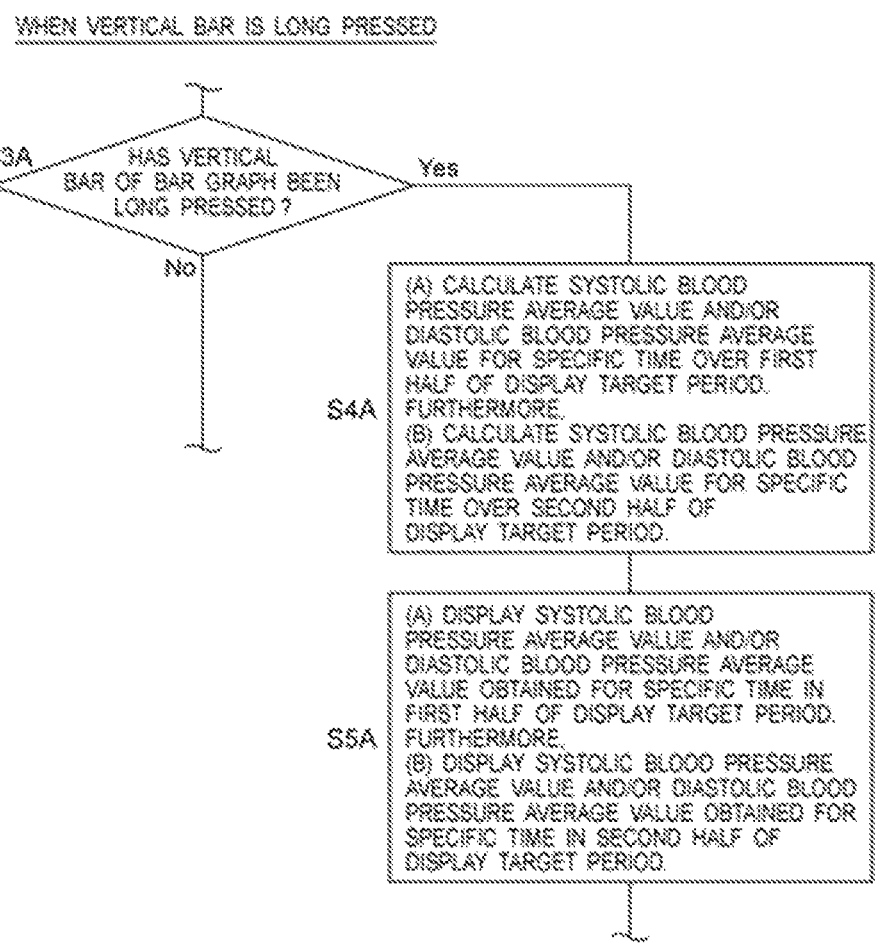
FIG. 24 is a view illustrating an operation flow in a case where a position corresponding to a vertical bar at a specific time is long pressed on the display unit of the personal terminal.
Figure 25:
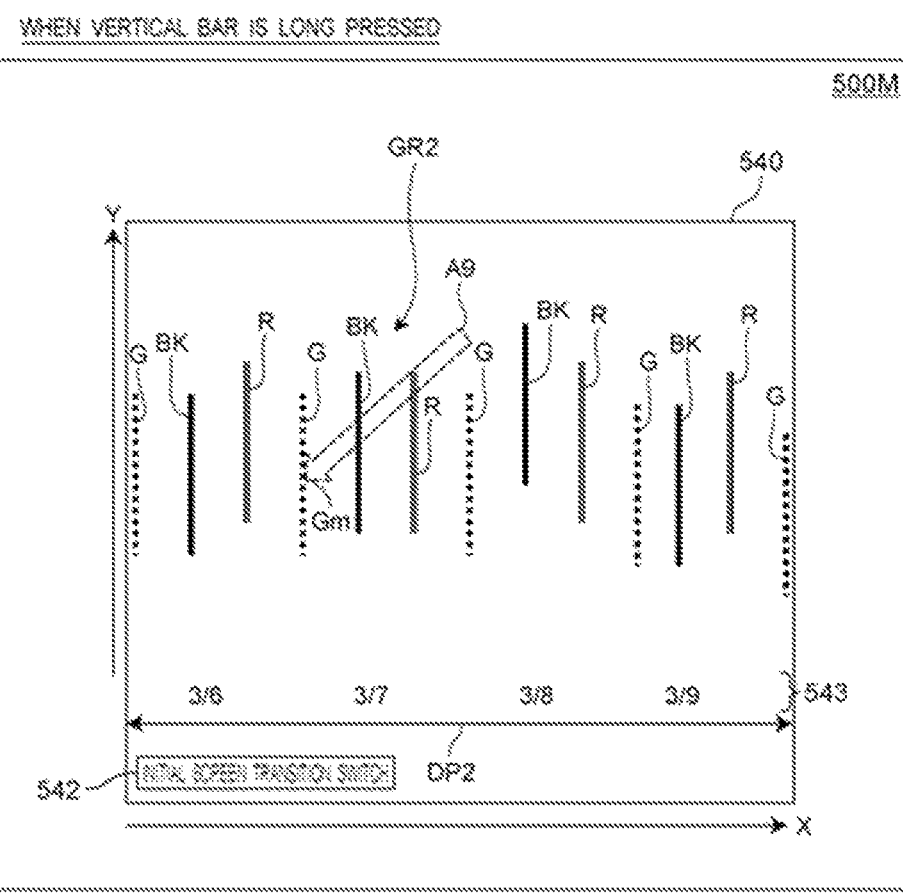
FIG. 25 is a view schematically illustrating a mode in which a position corresponding to a central portion of the vertical bar Bk at the specific time (first time) t1 is long pressed.

FIG. 24 illustrates an operation flow in a case where a position corresponding to the vertical bar Bk, R, or G at a specific time is long pressed on the display unit 540 of the personal terminal 500, in particular, steps (steps S3A to S5A) executed instead of steps S3 to S5 of the operation flow of FIG. 6A.

In Modification 4, after steps S1 and S2 of FIG. 6A, in step S3A of FIG. 24, the control unit 510 determines whether or not a position corresponding to the vertical bar Bk, R, or G at a specific time on the display unit 540 is long pressed with the touchpad 531. In this example, it is assumed that when the user operates the touchpad 531, as schematically indicated by long arrow A9 in FIG. 25, a position corresponding to the central portion Gm of the vertical bar G at the specific time t3 on the display unit 540 is long pressed. Instead of long press, sweep may be performed in the left direction (direction covering the first half of the display target period DP2) from the position corresponding to the central portion Gm.

Then, in step S4A of FIG. 24, the control unit 510 acts as the first calculation unit and obtains a systolic blood pressure average value (this is represented by reference sign "SBPaveF") and the diastolic blood pressure average value (this is represented by reference sign "DBPaveF") for the specific time t3 over the first half of the display target period DP2, and obtain the systolic blood pressure average value (this is represented by reference sign "SBPaveS") and the diastolic blood pressure average value (this is represented by reference sign "DBPaveS") for the specific time t3 over the second half of the display target period DP2.

Figure 26:
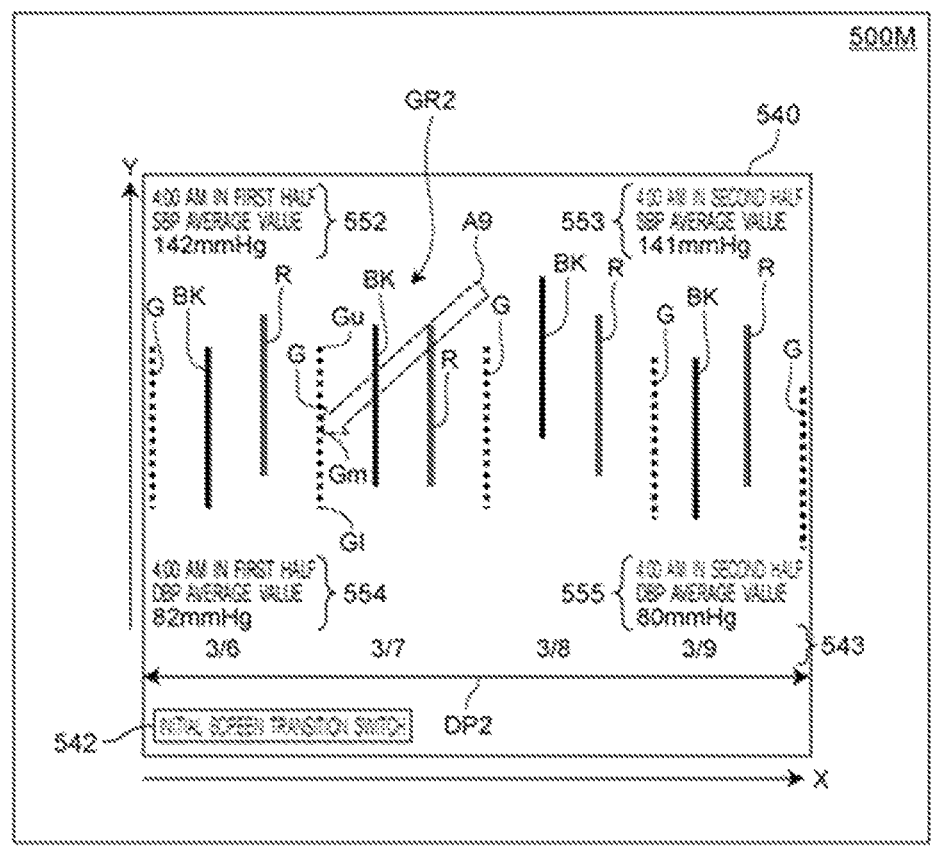
FIG. 26 is a view exemplifying content displayed on the display unit by the operation illustrated in FIG. 25.

Subsequently, in step S5A of FIG. 24, the control unit 510 acts as the first display control unit, and as illustrated in FIG. 26, pop-up displays, on the display unit 540, the systolic blood pressure average value SBPaveF and the diastolic blood pressure average value DBPaveF obtained for the specific time t3 in the first half of the display target period DP2 and the systolic blood pressure average value SBPaveS and the diastolic blood pressure average value DBPaveS obtained for the specific time t3 in the second half of the display target period DP2. In the example of FIG. 26, in areas 552 and 554 separated left upward and left downward from the bar graph GR2 on the display unit 540, the systolic blood pressure average value SBPaveF and the diastolic blood pressure average value DBPaveF for the specific time t3 over the first half of the display target period DP2 are pop-up displayed as digital values such as

"4:00 AM IN FIRST HALF

SBP AVERAGE VALUE 142 mmHg",

"4:00 AM IN FIRST HALF

DBP AVERAGE VALUE 82 mmHg". In areas 553 and 555 separated right upward and right downward from the bar graph GR2 on the display unit 540, the systolic blood pressure average value SBPaveS and the diastolic blood pressure average value DBPaveS for the specific time t3 over the second half of the display target period DP2 are pop-up displayed as digital values such as

"4:00 AM IN SECOND HALF

SBP AVERAGE VALUE 141 mmHg",

"4:00 AM IN SECOND HALF

DBP AVERAGE VALUE 80 mmHg". This allows the user to know the systolic blood pressure average values SBPaveF and SBPaveS and the diastolic blood pressure average values DBPaveF and DBPaveS for the specific time t3 by popping up them for each of the first half and the second half of the display target period DP2 with simple operation by long pressing (or sweeping) the vertical bar G at the specific time t3.

As known from FIG. 26, when the position corresponding to the upper end portion Gu of the vertical bar G at the specific time t3 is long pressed (or swept), the control unit 510 obtains only the systolic blood pressure average values SBPaveF and SBPaveS for the specific time t3 for each of the first half and the second half of the display target period DP2, and pop-up displays them on the display unit 540. When the position corresponding to the lower end portion Gl of the vertical bar G at the specific time t3 is long pressed (or swept), the control unit 510 obtains only the diastolic blood pressure average values DBPaveF and DBPaveS for the specific time t3 for each of the first half and the second half of the display target period DP2, and pop-up displays them on the display unit 540.

Modification 4 can be similarly applied even when what to be long pressed (or swept) is the vertical bar Bk corresponding to the time t1 or the vertical bar R corresponding to the time t2.

(Modification 5; Case where a Mark Representing an Event is Designated and a Vertical Bar is Designated)

Figure 28:
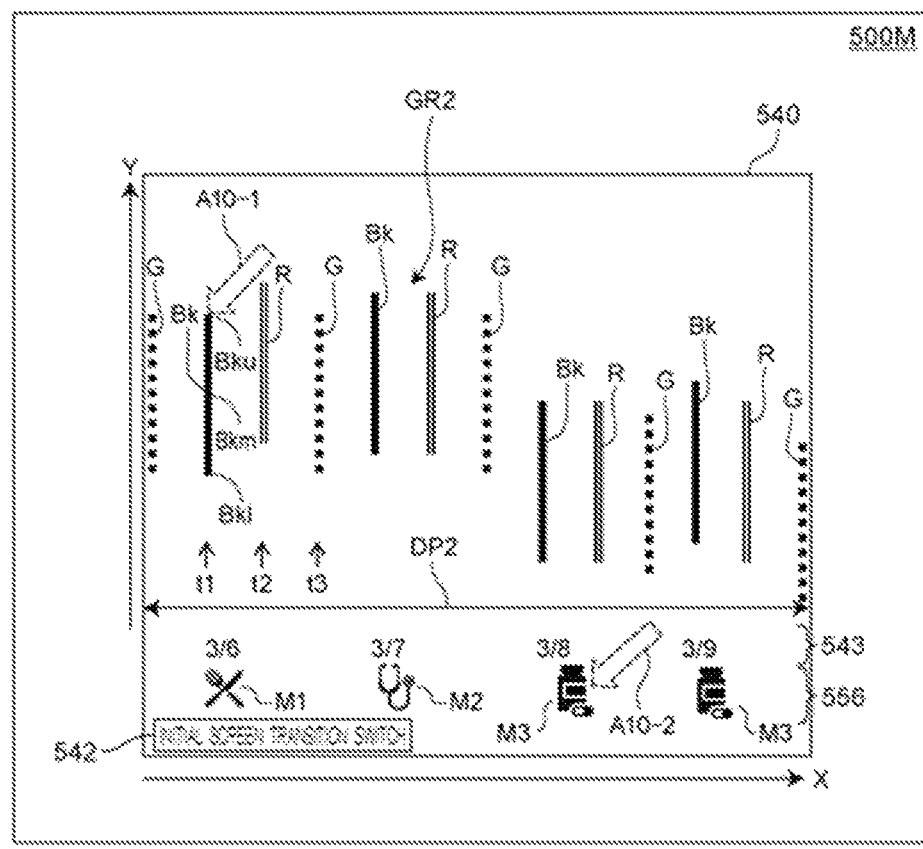
FIG. 28 is a view schematically illustrating a mode in which the mark M3 representing a specific event is designated and a position corresponding to the upper end portion of the vertical bar Bk at the specific time (first time) t1 is designated.

In Modification 5, an example is explained in which in step S2 of FIG. 6A, marks M1, M2, and M3 representing an event that occurred for each day on the subject are displayed in an area 556 along the lower side of the date display area 543 along the bar graph GR2 as another initial screen in the display unit 540 as exemplified in FIG. 28. Here, the mark M1 including a symbol of a fork and a knife indicates that the subject ate out as an event. The mark M2 including a symbol of a stethoscope indicates that the subject received a medical examination as an event. The mark M3 including a symbol of a medicine bottle and a tablet indicates that the subject took medicine as an event. In this example, the mark M1 representing eating out is displayed for only one day (March 6), the mark M2 representing receiving a medical examination is displayed for only one day (March 7), and the mark M3 representing taking medicine is displayed for two days (March 8 and March 9). Due to this, in this example, it is seen that the subject ate out on March 6, received a medical examination on March 7, and took medicine on March 8 and March 9, respectively. In the bar graph GR2 in FIG. 28, as known from the positions of the vertical bars Bk, R, and G regarding the vertical direction Y, the blood pressure values of the days (March 8 and March 9) on which the subject took medicine become lower than the blood pressure values of the remaining days (March 6 and March 7).

It is assumed that the event that occurred on each day on the subject is stored in the memory 520 in advance by being manually input via the operation unit 530, being input by voice recognition using the speech analysis/recognition unit 580, and/or being determined based on positional data of the personal terminal 500 generated by the GPS unit 570 (for example, when the subject carrying the personal terminal 500 stays in a restaurant, a hospital, or the like other than his/her home for 30 minutes or more, it is determined that an event such as eating out or receiving a medical examination has occurred).

Figure 27:
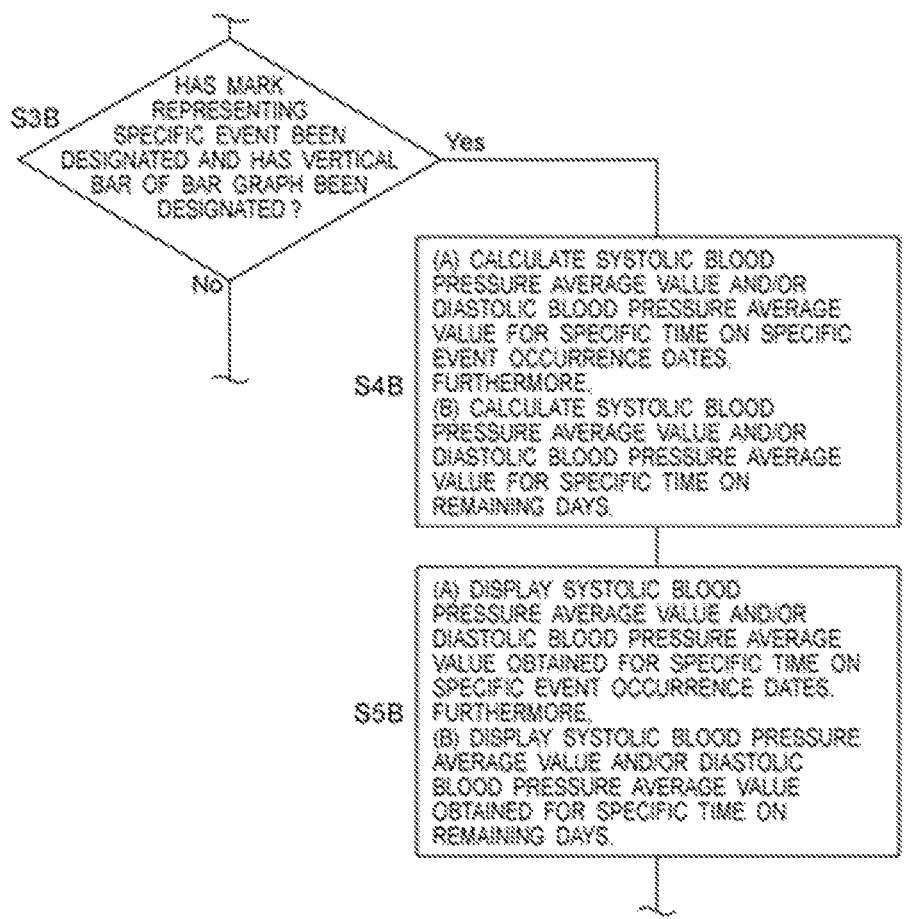
FIG. 27 is a view illustrating an operation flow in a case where a mark representing an event is designated and a position corresponding to a vertical bar at a specific time is designated on the display unit of the personal terminal.

FIG. 27 illustrates an operation flow in a case where a mark representing an event is designated and a position corresponding to a vertical bar at a specific time is designated on the display unit 540 of the personal terminal 500, in particular, steps (steps S3B to S5B) executed instead of steps S3 to S5 of the operation flow of FIG. 6A.

In Modification 5, after steps S1 and S2 of FIG. 6A, in step S3B of FIG. 27, the control unit 510 determines whether or not a mark representing an event on the display unit 540 is designated with the touchpad 531 and a position corresponding to the vertical bar Bk, R, or G at a specific time is designated. In this example, it is assumed that when the user operates the touchpad 531, as schematically indicated by arrow A10-2 in FIG. 28, the mark M3 (any of the marks M3 displayed for two days) representing the event of taking medicine is designated as a specific event, and as schematically indicated by arrow A10-1, a position corresponding to the upper end portion Bku of the vertical bar Bk at the specific time t1 on the display unit 540 is designated.

Then, in step S4B of FIG. 27, the control unit 510 acts as the first calculation unit and obtains a systolic blood pressure average value (this is represented by reference sign "SBPaveE") for the specific time t1 on the specific event occurrence dates (in this example, March 8 and March 9) on which the event of taking medicine occurred (step S4B(a)). Along with this, the control unit 510 works as the first calculation unit and obtains a systolic blood pressure average value (this is represented by reference sign "SBPaveR") for the specific time t1 on the remaining days (in this example, March 6 and March 7) in which the specific event occurrence dates are excluded from the display target period DP2 (step S4B(b)).

Here, assuming that the specific event occurrence dates are m days (m is a natural number of n or less) within the display target period DP2 (n days with n as a natural number) and the systolic blood pressure values at the specific time t1 on the specific event occurrence dates are SBP1E, SBP2E, . . . , and SBPmE, the systolic blood pressure average value SBPaveE for the specific time t1 on the specific event occurrence dates is defined by (SBP1E+SBP2E+ . . . +SBPmE)/m (in the present embodiment, this definition is extended to the case of m=1). Similarly, assuming that the remaining days are k days (k=n−m) within the display target period DP2 (n days with n as a natural number) and the systolic blood pressure values at the specific time t1 on the remaining days are SBP1R, SBP2R, . . . , and SBPkR, the systolic blood pressure average value SBPaveR for the specific time t1 on the remaining days is defined by (SBP1R+SBP2R+ . . . +SBPkR)/k (in the present embodiment, this definition is extended to the case of k=1). In a case of k=0, since there is no remaining day, the systolic blood pressure average value SBPaveR is not calculated nor displayed.

Figure 29:
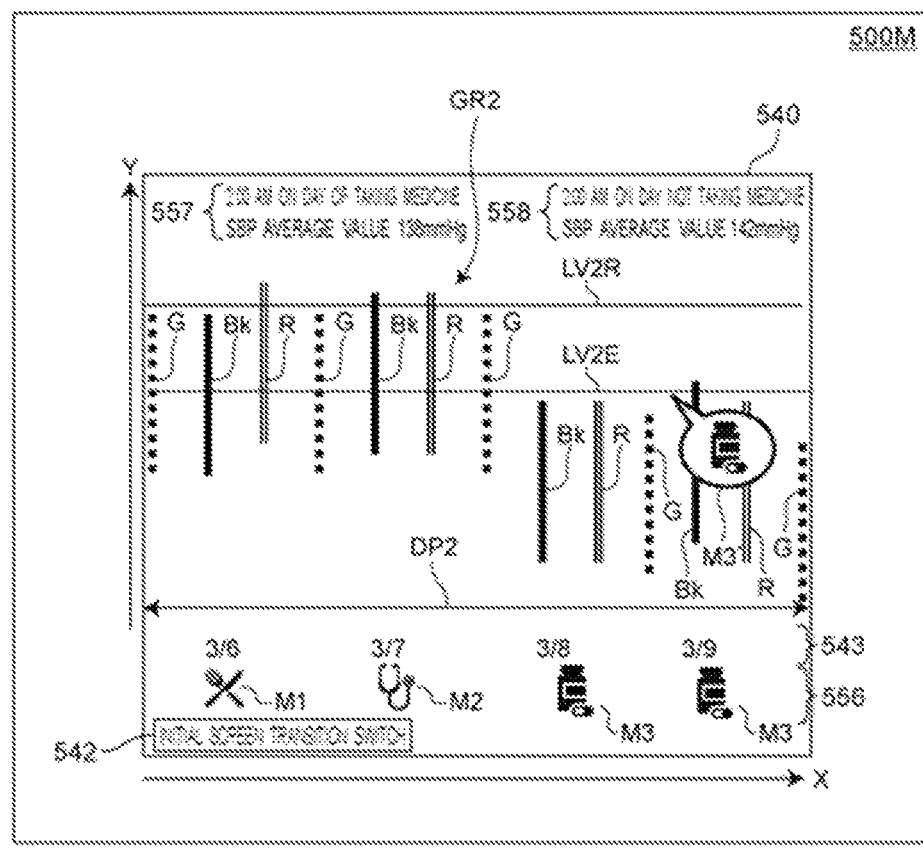
FIG. 29 is a view exemplifying content displayed on the display unit by the operation illustrated in FIG. 28.

Subsequently, in step S5B of FIG. 27, the control unit 510 acts as the first display control unit, and displays the systolic blood pressure average value SBPaveE obtained for the specific time t1 on the specific event occurrence dates and the systolic blood pressure average value SBPaveR obtained for the specific time t1 on the remaining days on the display unit 540 together with the bar graph GR2 as illustrated in FIG. 29 (steps S5B(a) and (b)). In the example of FIG. 29, in areas 557 and 558 separated left upward and right upward from the bar graph GR2 on the display unit 540, the systolic blood pressure average value SBPaveE obtained for the specific time t1 on specific event occurrence dates and the systolic blood pressure average value SBPaveR obtained for the specific time t1 on the remaining day are pop-up displayed as digital values such as "2:00 AM ON DAY OF TAKING MEDICINE
SBP AVERAGE VALUE 138 mmHg",
"2:00 AM ON DAY NOT TAKING MEDICINE
SBP AVERAGE VALUE 142 mmHg". This allows the user to know by comparison by causing the systolic blood pressure average value SBPaveE for the specific time t1 on the specific event occurrence dates and the systolic blood pressure average value SBPaveR for the specific time t1 on the remaining days to be displayed on the display unit 540 with simple operation. Here, when pinch in and pinch out are executed, the display target period DP is changed, the calculation result also varies accordingly, and the varied calculation result is reflected in the pop-up display.

The date illustrated on the leftmost of the display target period DP (March 6 in the case of FIG. 11) is referred to as beginning end date, and the date illustrated on the rightmost (March 9 in the case of FIG. 11) is referred to as terminal end date. In a case of pinching in with two fingers, when the user fixes the left finger and slides the right finger leftward on the screen, the beginning end date is fixed, the terminal end date is shifted leftward, and more days are included in the display target period DP. When the user fixes the right finger and slides the left finger rightward on the screen, the terminal end date is fixed, the beginning end date is shifted in rightward, and more days are included in the display target period DP. Then, when the user slides both fingers at the same time in the direction of approaching each other, the beginning end date is shifted rightward, the terminal end date is shifted leftward, and more days are included in the display target period DP. Conversely, in the case of pinching out, the user can similarly perform operation of fixing the beginning end date and shifting only the terminal end date, fixing the terminal end date and shifting only the beginning end date, or shifting both the beginning end date and the terminal end date. For example, in FIG. 11, when the user performs operation of pinch in of fixing the beginning end date and shifting only the terminal end date, the third day, the fourth day, the fifth day . . . from the fixed March 6 are sequentially included in the display target period DP, and accordingly, the systolic blood pressure average value SBPave indicated in the area 545 sequentially changes as an average value for 3 days, an average value for 4 days, an average value for 5 days, . . . . Here, in a case where treatment (dosing, surgery, and the like) is performed on March 6, the user can easily find the day on which a change is seen in the average value, that is, the day on which an effect of the treatment appears. This is because a daily change in the blood pressure value depends on daily living environment, but a change in the blood pressure average value strongly reflects a physical change.

Instead of performing one-side fixed pinch in and pinch out with two fingers, pinch-in buttons 604 and 612 and pinch-out buttons 602 and 614 may be provided. In this example, the pinch-in button 604 includes a leftward thick line arrow displayed in the vicinity of the right end of the display screen along the bar graph GR2. The pinch-in button 612 includes a rightward thick line arrow displayed in the vicinity of the left end of the display screen along the bar graph GR2. The pinch-out button 602 includes a rightward thick line arrow displayed in the vicinity of the right end of the display screen along the bar graph GR2. The pinch-out button 614 includes a leftward thick line arrow displayed in the vicinity of the left end of the display screen along the bar graph GR2. When the user presses the pinch-out button 602, the beginning end date is fixed and the terminal end date is shifted to the right side, and fewer days are displayed. When the user presses the pinch-in button 604, the beginning end date is fixed and the terminal end date is shifted to the left side, and more days are displayed. When the user presses the pinch-out button 614, the terminal end date is fixed and the beginning end date is shifted to the left side, and fewer days are displayed. When the user presses the pinch-in button 612, the terminal end date is fixed and the beginning end date is shifted to the right side, and more days are displayed. This allows the user to easily perform increment or decrement for each day.

Along with this, the control unit 510 acts as the first display control unit, and pop-up displays, on the display unit 540, the systolic blood pressure average value SBPaveE obtained for the specific time t1 on the specific event occurrence dates and the systolic blood pressure average value SBPaveR obtained for the specific time t1 on the remaining days as horizontal bars LV2E and LV2R, respectively, superimposed on the bar graph GR2. The horizontal bar LV2E is provided with a mark M3' representing, as a balloon, the mark M3 including a symbol of a medicine bottle and a tablet. This allows the user to intuitively grasp the respective positions of the systolic blood pressure average value SBPaveE and the systolic blood pressure average value SBPaveR with respect to the bar graph GR2. In this example, the horizontal bar LV2E for the specific event occurrence dates on which the event of taking medicine occurred is displayed at a position lower than the horizontal bar LV2R for the remaining days. Therefore, the user can grasp that the height difference between the horizontal bar LV2E and the horizontal bar LV2R corresponds to the effect of taking medicine.

In a case where the mark M3 representing an event is designated and a position corresponding to the lower end portion Bk1 (see FIG. 28) of the vertical bar Bk at the specific time t1 is designated in step S3B of FIG. 27, the control unit 510 acts as the first calculation unit, in step S4B of FIG. 27, and obtains the diastolic blood pressure average value (this is represented by reference sign "DBPaveE") for the specific time t1 on the specific event occurrence dates (in this example, March 8 and March 9) on which the specific event occurred and the diastolic blood pressure average value (this is represented by reference sign "DBPaveR") for the specific time t1 on the remaining days (in this example, March 6 and March 7) in which the specific event occurrence dates are excluded from the display target period DP2. Then, in step S5B of FIG. 27, the control unit 510 acts as the first display control unit, and pop-up displays, on the display unit 540, the diastolic blood pressure average value DBPaveE obtained for the specific time t1 on the specific event occurrence dates and the diastolic blood pressure average value DBPaveR obtained for the specific time t1 on the remaining days.

Here, assuming that the specific event occurrence dates are m days within the display target period (n days) and the diastolic blood pressure value at the specific time t1 on the specific event occurrence dates are DBP1E, DBP2E, . . . , and DBPmE, the diastolic blood pressure average value DBPaveE for the specific time t1 on the specific event occurrence dates is defined by (DBP1E+DBP2E+ . . . +DBPmE)/m (in the present embodiment, this definition is extended to the case of m=1). Similarly, assuming that the remaining days are k days (k=n−m) within the display target period DP2 (n days with n as a natural number) and the diastolic blood pressure values at the specific time t1 on the remaining days are DBP1R, DBP2R, . . . , and DBPkR, the diastolic blood pressure average value DBPaveR for the specific time t1 on the remaining days is defined by (DBP1R+DBP2R+ . . . +DBPkR)/k (in the present embodiment, this definition is extended to the case of k=1). In a case of k=0, since there is no remaining day, the diastolic blood pressure average value DBPaveR is not calculated nor displayed.

In a case where the mark M3 representing an event is designated and a position corresponding to the central portion Bkm (see FIG. 28) of the vertical bar Bk at the specific time t1 is designated in step S3B of FIG. 27, the control unit 510 acts as the first calculation unit, in step S4B of FIG. 27, and obtains the systolic blood pressure average value SBPaveE and the diastolic blood pressure average value DBPaveE for the specific time t1 on the specific event occurrence dates (in this example, March 8 and March 9) on which the specific event occurred and the systolic blood pressure average value SBPaveR and the diastolic blood pressure average value DBPaveR for the specific time t1 on the remaining days (in this example, March 6 and March 7) in which the specific event occurrence dates are excluded from the display target period DP2. Then, in step S5B of FIG. 27, the control unit 510 acts as the first display control unit, and pop-up displays, on the display unit 540, the systolic blood pressure average value SBPaveE and the diastolic blood pressure average value DBPaveE obtained for the specific time t1 on the specific event occurrence dates and the systolic blood pressure average value SBPaveR and the diastolic blood pressure average value DBPaveR obtained for the specific time t1 on the remaining day.

In step S5B of FIG. 27, the control unit 510 may act as the first display control unit and pop-up display, on the display unit 540, the systolic blood pressure average value SBPave and/or the diastolic blood pressure average value DBPave for the specific time t1 over the display target period DP2 (entire) together with the above.

Modification 5 can be similarly applied even when what to be designated together with a mark representing a specific event is the vertical bar R corresponding to the time t2 or the vertical bar G corresponding to the time t3.

In Modification 5, the events include eating out, receiving a medical examination, and taking medicine, but are not limited to this. The event may include working (or resting) and arrival of a specific day of the week (for example, Monday). What to correspond to the "event" can be variably set by the user (subject, doctor, and the like).

In the above-described embodiment, the blood-pressure-related data measured by the sphygmomanometer 400 is temporarily stored in the database 321 of the server 300, and the personal terminal 500 downloads the blood-pressure-related data. However, the present invention is not limited to this. The blood-pressure-related data measured by the sphygmomanometer 400 may be directly received by the personal terminal 500 via the network 900 and stored in the memory 520.

In the above-described embodiment, the above-described method for displaying blood-pressure-related information is executed by the subject as the user operating the personal terminal 500. However, the present invention is not limited to this. The above-described method for displaying blood-pressure-related information may be executed, for example, by a doctor as a user operating the hospital terminal 200.

Figure 30:
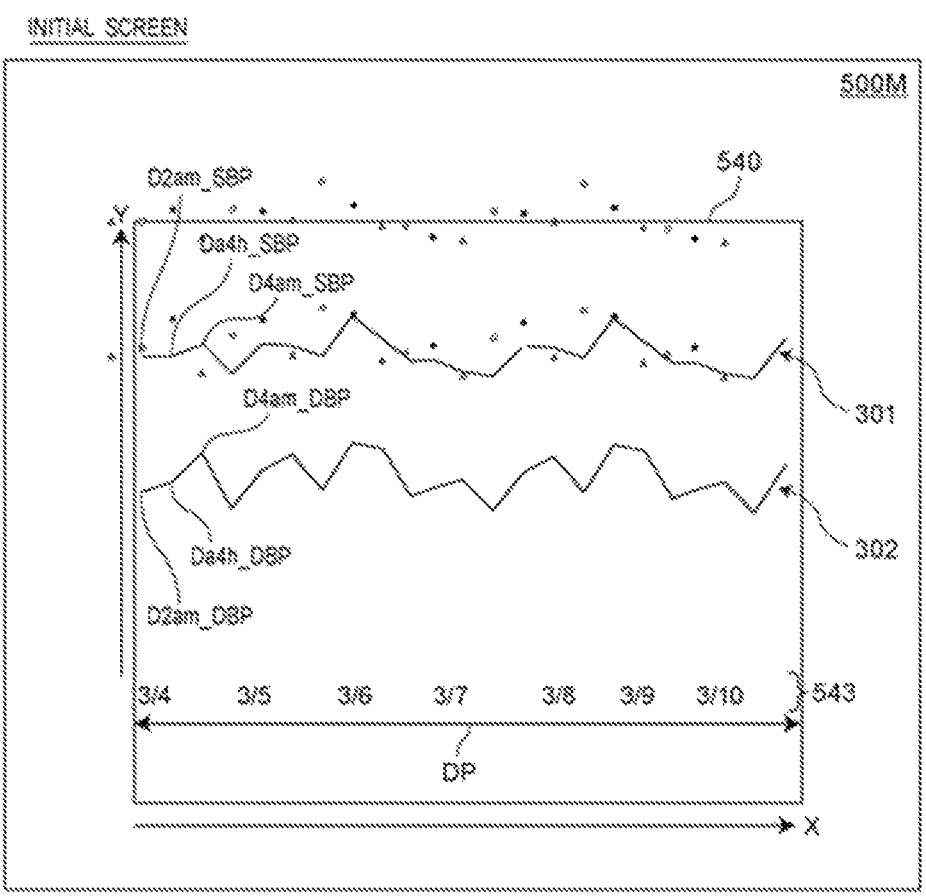
FIG. 30 is a view exemplifying an initial screen different from the initial screen illustrated in FIG. 7.

In the above-described embodiment, the change in the blood pressure value is displayed using the bar graph, but as a variation of the embodiment, a line graph may be used in place of the bar graph. FIG. 30 exemplifies an initial screen different from the initial screen illustrated in FIG. 7 including an SBP line graph 301 and a DBP line graph 302 as line graphs. Specifically, the SBP line graph 301 is created by sequentially connecting, with line segments, the point (reference sign "D2am_SBP") corresponding to the SBP at the time t1, the point (reference sign "Da4h_SBP") corresponding to the SBP at the time t2, the point (reference sign "D4am_SBP") corresponding to the SBP at the time t3, and . . . . The DBP line graph 302 is created by sequentially connecting, with line segments, the point (reference sign "D2am_DBP") corresponding to the DBP at the time t1, the point (reference sign "Da4h_DBP") corresponding to the DBP at the time t2, the point (reference sign "D4am_DBP") corresponding to the DBP at the time t3, and . . . . Similarly to the operation on the bar graph described above, when the user performs operation of designating (touching) a position (point) corresponding to a specific time of the SBP line graph 301 and the DBP line graph 302, the SBP average value and/or the DBP average value is pop-up displayed on the display unit 540. Also in this case, the display target period DP can be variably set by the operation of pinch in and pinch out described above.

The above-described method for displaying blood-pressure-related information may be recorded as software (a computer program) on a non-transitory recording medium capable of storing data, such as a compact disc (CD), a digital universal disc (DVD), or a flash memory. By installing software recorded on such a recording medium in a substantial computer device such as a personal computer, a personal digital assistant (PDA), or a smartphone, the computer device can be caused to execute the above-described method for displaying blood-pressure-related information.

As described above, a device for displaying blood-pressure-related information of the present disclosure is a device that displays information related to blood pressure of a subject on a display screen, the device comprising:

a data input unit that receives, for a subject, blood pressure value data including a systolic blood pressure value and a diastolic blood pressure value measured at least at a predetermined plurality of times of a day for each day over a plurality of days;

a storage unit that is capable of storing the blood pressure value data;

a pointing device that is capable of operation of designating a position on the display screen;

an initial display control unit that sets date and time in a horizontal direction and blood pressure in a vertical direction on the display screen, and displays, as a bar graph, a change in a blood pressure value over a display target period corresponding to all or some of the plurality of days with vertical bars each formed by connecting the systolic blood pressure value and the diastolic blood pressure value for each time and arranged in a horizontal direction;

a first calculation unit that, when a position corresponding to a vertical bar at a specific time on the display screen is designated with the pointing device during display of the bar graph, averages data of the systolic blood pressure value measured for each day at the specific time over the display target period to obtain a systolic blood pressure average value for the specific time, and/or averages data of the diastolic blood pressure value measured for each day at the specific time over the display target period to obtain a diastolic blood pressure average value for the specific time, according to the position designated; and a first display control unit that displays, on the display screen, the systolic blood pressure average value and/or the diastolic blood pressure average value obtained for the specific time together with the bar graph.

In the present description, "time" in "a predetermined plurality of times of a day" means a daily time, that is, a time for which a date is not considered. For example, the "time" at which the blood pressure value is measured refers to 2:00 AM, 4:00 AM, and the like, but is not limited to this. The "time" may include a time relatively set as, for example, "x hours since bedding down" (for example, x=4).

The "plurality of days" typically refers to a period such as two weeks or one month.

The "blood pressure value data" includes the systolic blood pressure value and the diastolic blood pressure value. Other than them, data of the pulse rate measured together with the blood pressure value may be included.

An initial display control unit "sets~in the horizontal direction and sets~in the vertical direction" means that corresponding amounts (date and time, blood pressure, and the like) are set as the horizontal axis and the vertical axis, respectively, in a state where the user (the subject and medical personnel such as a doctor or a nurse) views the display screen. However, an axis (straight line), a scale, and the like are not necessarily displayed on the display screen.

A "display target period" is a period presented in the horizontal direction on the display screen, and typically refers to a period such as several days or one week.

A "pointing device" is a device for a user to perform an operation of designating a position on the display screen, and may be a mouse, a touchpad placed on the display screen (the user designates a position on the pad with a finger or a pen), or the like.

Assuming that the display target period is n days (n is a natural number) and the blood pressure values at the specific time are BP1, BP2, . . . , and BPn, the "blood pressure average value" over the display target period is defined by (BP1+BP2+ . . . +BPn)/n (in the present description, this definition is extended to the case of n=1).

"The systolic blood pressure average value and/or the diastolic blood pressure average value" means a blood pressure average value of any one of the systolic blood pressure average value and the diastolic blood pressure average value, or blood pressure average values of the both.

In the device for displaying blood-pressure-related information of the present disclosure, a data input unit receives, for a subject, blood pressure value data including a systolic blood pressure value and a diastolic blood pressure value measured at least at a predetermined plurality of times of a day for each day over a plurality of days. The blood pressure value data is stored in the storage unit. The initial display control unit sets the date and time in the horizontal direction and the blood pressure in the vertical direction on the display screen, and displays, as a bar graph, a change in the blood pressure value over a display target period corresponding to all or some of the plurality of days with vertical bars each formed by connecting the systolic blood pressure value and the diastolic blood pressure value for each time and arranged in the horizontal direction. During display of the bar graph, the user operates the pointing device to designate a position corresponding to a vertical bar at a specific time on the display screen. Then, according to the position designated, a first calculation unit averages the data of the systolic blood pressure value measured at the specific time over the display target period to obtain a systolic blood pressure average value for the specific time, and/or averages the data of the diastolic blood pressure value measured at the specific time over the display target period to obtain a diastolic blood pressure average value for the specific time. A first display control unit displays, on the display screen, the systolic blood pressure average value and/or the diastolic blood pressure average value obtained for the specific time together with the bar graph. Therefore, according to the device for displaying blood-pressure-related information, the blood pressure average value over a plurality of days (the display target period) at a specific time can be displayed on the display screen with a simple operation (that is, operation by the user designating a position corresponding to a vertical bar at a specific time on the display screen with the pointing device).

In the device for displaying blood-pressure-related information according to one embodiment,
  the first display control unit displays, on the display screen, the systolic blood pressure average value and/or the diastolic blood pressure average value obtained for the specific time as a digital value, and also graphically as a horizontal bar superimposed on the bar graph.

In the device for displaying blood-pressure-related information of this one embodiment, the systolic blood pressure average value and/or the diastolic blood pressure average value obtained for the specific time is displayed as a digital value on the display screen, and therefore the user can accurately know the systolic blood pressure average value and/or the diastolic blood pressure average value. In the device for displaying blood-pressure-related information of this one embodiment, the systolic blood pressure average value and/or the diastolic blood pressure average value obtained for the specific time is graphically displayed as a horizontal bar superimposed on the bar graph (presenting a change in the blood pressure value over the display target period) on the display screen, and therefore the user can intuitively grasp the positioning of the systolic blood pressure average value and/or the diastolic blood pressure average value with respect to the bar graph.

In the device for displaying blood-pressure-related information according to one embodiment,
  the plurality of times include at least two times of a set time and an elapsed time since bedding down.

The "set time" refers to, for example, 2:00 AM, 4:00 AM, and the like at night. The "elapsed time since bedding down" means the time, for example, x hours (for example, x=4) after the subject bedding down (taking a sleeping position).

In the device for displaying blood-pressure-related information of this one embodiment, a blood pressure average value (the systolic blood pressure average value and/or the diastolic blood pressure average value) obtained for, as the specific time, at least two times of the set time and the elapsed time since bedding down can be displayed on the display screen together with the bar graph. The blood pressure at these times has recently attracted attention in relation to cardiovascular risk. Therefore, according to the device for displaying blood-pressure-related information of this one embodiment, it is possible to display a blood pressure average value (the systolic blood pressure average value and/or the diastolic blood pressure average value) for the times attracting attention in relation to cardiovascular risk.

In the device for displaying blood-pressure-related information according to one embodiment,
  when a position corresponding to an upper end portion of a vertical bar at a specific time on the display screen is designated with the pointing device, the first calculation unit obtains the systolic blood pressure average value for the specific time according to the position designated, and the first display control unit displays the systolic blood pressure average value obtained for the specific time on the display screen together with the bar graph,
  when a position corresponding to a lower end portion of a vertical bar at a specific time on the display screen is designated with the pointing device, the first calculation unit obtains the diastolic blood pressure average value for the specific time according to the position designated, and the first display control unit displays the diastolic blood pressure average value obtained for the specific time on the display screen together with the bar graph, and
  when a position corresponding to a central portion of a vertical bar at a specific time on the display screen is designated with the pointing device, the first calculation unit obtains the systolic blood pressure average value and the diastolic blood pressure average value for the specific time according to the position designated, and the first display control unit displays the systolic blood pressure average value and the diastolic blood pressure average value obtained for the specific time on the display screen together with the bar graph.

Here, an "upper end portion" and a "lower end portion" of the vertical bar are not limited to the upper end and the lower end (end points) themselves, respectively, and may include a certain range (for example, a range of about 10% of the entire length of the vertical bar) from the upper end and the lower end, respectively. A "central portion" of the vertical bar refers to a portion other than the "upper end portion" and the "lower end portion" of the entire length of the vertical bar.

In the device for displaying blood-pressure-related information of this one embodiment, the user operates the pointing device to designate a position corresponding to the upper end portion, the lower end portion, or the central portion of the vertical bar at a specific time on the display screen. When the position corresponding to the upper end portion of the vertical bar at the specific time on the display screen is designated with the pointing device, the first calculation unit obtains the systolic blood pressure average value for the specific time according to the position designated, and the first display control unit displays the systolic blood pressure average value obtained for the specific time on the display screen together with the bar graph. When the position corresponding to the lower end portion of the vertical bar at the specific time on the display screen is designated with the pointing device, the first calculation unit obtains the diastolic blood pressure average value for the specific time according to the position designated, and the first display control unit displays the diastolic blood pressure average value obtained for the specific time on the display screen together with the bar graph. Here, of each vertical bar, the upper end portion represents a systolic blood pressure value, and the lower end represents a diastolic blood pressure value. Furthermore, when the position corresponding to the central portion of the vertical bar at the specific time on the display screen is designated with the pointing device, the first calculation unit obtains the systolic blood pressure average value and the diastolic blood pressure average value for the specific time according to the position designated, and the first display control unit displays the systolic blood pressure average value and the diastolic blood pressure average value obtained for the specific time on the display screen together with the bar graph. Therefore, when the user designates a portion of each vertical bar representing the blood pressure value corresponding to the blood pressure average value that he/she desires to display, it is possible to cause the blood pressure average value that he/she desires to display to be displayed. That is, the user can cause the blood pressure average value that he/she desires to display to be displayed with operation according to his/her natural sense.

In the device for displaying blood-pressure-related information according to one embodiment,
when a position corresponding to one end portion of any of an upper end portion and a lower end portion of the vertical bar at the specific time on the display screen is designated with the pointing device, and then a position corresponding to other end portion of the vertical bar is consecutively designated with the pointing device, the first display control unit displays, on the display screen, a blood pressure average value corresponding to the other end portion for the specific time in addition to a blood pressure average value corresponding to the one end portion for the specific time.

In the present description, "consecutively designate" refers to designation regarded to be designation substantially related to previous designation such as designation within one second, for example.

In the device for displaying blood-pressure-related information of this one embodiment, the user operates the pointing device to designate a position corresponding to one end portion of any of the upper end portion and the lower end portion of the vertical bar at the specific time on the display screen, and then operates the pointing device to consecutively designate a position corresponding to other end portion of the vertical bar. Then, the first display control unit displays, on the display screen, the blood pressure average value corresponding to the other end portion for the specific time in addition to the blood pressure average value corresponding to the one end portion for the specific time. Therefore, the user can cause both blood pressure average values (here, the systolic blood pressure average value and the diastolic blood pressure average value for the specific time) to be displayed with operation according to his/her natural sense.

In the device for displaying blood-pressure-related information according to one embodiment,
when a position corresponding to an upper end portion, a lower end portion, or a central portion of the vertical bar at the specific time on the display screen is designated with the pointing device, and then a position corresponding to a same portion of a vertical bar at another time as that of the vertical bar at the specific time is consecutively designated with the pointing device, the first display control unit displays, on the display screen, a blood pressure average value corresponding to the same portion for the another time in addition to a blood pressure average value corresponding to the upper end portion, the lower end portion, or the central portion for the specific time.

In the device for displaying blood-pressure-related information of this one embodiment, the user operates the pointing device to designate a position corresponding to the upper end portion, the lower end portion, or the central portion of the vertical bar at the specific time on the display screen, and then operates the pointing device to consecutively designate a position corresponding to the same portion of a vertical bar at another time as that of the vertical bar at the specific time. Then, the first display control unit displays, on the display screen, the blood pressure average value corresponding to the same portion for the another time in addition to the blood pressure average value corresponding to the upper end portion, the lower end portion, or the central portion for the specific time. Therefore, the user can cause the blood pressure average value for both times to be displayed with operation according to his/her natural sense.

In the device for displaying blood-pressure-related information according to one embodiment,
when a specific position on the display screen is long pressed with the pointing device, the first display control unit increases an amount of information to be displayed together with the bar graph on the display screen as compared with an amount of information to be displayed with short press.

In the present description, "long press" means that designation (press) with the pointing device is continuously continued for a certain period of time (for example, 3 seconds) or more. "Short press" is normal designation, and means that designation (press) with the pointing device ends within a certain time (for example, 1 second).

"Increase the amount of information" means that, for example, with the "short press", only the systolic blood pressure average value for a specific time is displayed together with the bar graph, whereas with the "long press", a standard deviation value is displayed together with the systolic blood pressure average value for the specific time.

In the device for displaying blood-pressure-related information of this one embodiment, the user operates the pointing device to long-press a specific position on the display screen. Then, the first display control unit increases the amount of information to be displayed together with the bar graph on the display screen as compared with the amount of information to be displayed with the short press. Therefore, the user can increase the amount of information to be displayed with operation according to his/her natural sense.

In the device for displaying blood-pressure-related information according to one embodiment, when a position corresponding to a vertical bar at a specific time on the display screen is long pressed with the pointing device, the first calculation unit obtains a systolic blood pressure average value and/or a diastolic blood pressure average value for the specific time over a first half of the display target period, and obtains a systolic blood pressure average value and/or a diastolic blood pressure average value for the specific time over a second half of the display target period, and the first display control unit displays, on the display screen, the systolic blood pressure average value and/or the diastolic blood pressure average value obtained for the specific time in a first half of the display target period, and the systolic blood pressure average value and/or the diastolic blood pressure average value obtained for the specific time in a second half of the display target period.

In the device for displaying blood-pressure-related information of this one embodiment, the user operates the pointing device to long-press a position corresponding to a vertical bar at a specific time on the display screen. Then, the first calculation unit obtains a systolic blood pressure average value and/or a diastolic blood pressure average value for the specific time over the first half of the display target period, and obtains a systolic blood pressure average value and/or a diastolic blood pressure average value for the specific time over the second half of the display target period. The first display control unit displays, on the display screen, the systolic blood pressure average value and/or the diastolic blood pressure average value obtained for the specific time in the first half of the display target period, and the systolic blood pressure average value and/or the diastolic blood pressure average value obtained for the specific time in the second half of the display target period. Therefore, by long-pressing the vertical bar at a specific time, the user can cause, with a simple operation, a systolic blood pressure average value and/or a diastolic blood pressure average value for the first half and the second half of the display target period to be displayed.

According to whether any position corresponding to the upper end portion, the lower end portion, or the central portion of the vertical bar at the specific time is long pressed, the first calculation unit may obtain only the systolic blood pressure average value, only the diastolic blood pressure average value, or both the systolic blood pressure average value and the diastolic blood pressure average value for the specific time for each of the first half and the second half of the display target period, and accordingly, the first display control unit may display only the systolic blood pressure average value, only the diastolic blood pressure average value, or both the systolic blood pressure average value and the diastolic blood pressure average value obtained for the specific time for each of the first half and the second half of the display target period.

In the device for displaying blood-pressure-related information according to one embodiment, the initial display control unit displays a mark representing an event that occurred for each day on the subject along the bar graph on the display screen, when the mark representing a specific event is designated and a position corresponding to the vertical bar at the specific time is designated with the pointing device on the display screen, the first calculation unit obtains a systolic blood pressure average value and/or a diastolic blood pressure average value for the specific time on specific event occurrence dates on which the specific event occurred, and the first display control unit display the systolic blood pressure average value and/or the diastolic blood pressure average value obtained for the specific time on the specific event occurrence dates on the display screen together with the bar graph.

An "event" refers to, for example, taking medicine, receiving a medical examination, eating out, working (or resting), arrival of a specific day of the week (for example, Monday), and the like. What corresponds to the "event" can be variably set by the user.

"Specific event occurrence dates" means dates on each of which a specific event occurred.

Assuming that the specific event occurrence dates are m days (m is a natural number of n or less) within the display target period (n days with n as a natural number) and the blood pressure values at the specific time on the specific event occurrence dates are BP1E, BP2E, . . . , and BPmE, the "blood pressure average value" for a specific time on the specific event occurrence dates is defined by (BP1E+BP2E+ . . . +BPmE)/m (in the present embodiment, this definition is extended to the case of m=1).

In the device for displaying blood-pressure-related information of this one embodiment, the initial display control unit displays a mark representing an event that occurred for each day on the subject along the bar graph on the display screen. In a case where the mark representing a specific event is displayed on the display screen, the user operates the pointing device to designate the mark representing the specific event and designate a position corresponding to the vertical bar at the specific time. Then, the first calculation unit obtains a systolic blood pressure average value and/or a diastolic blood pressure average value for the specific time on the specific event occurrence dates on which the specific event occurred. The first display control unit displays the systolic blood pressure average value and/or the diastolic blood pressure average value obtained for the specific time on the specific event occurrence dates on the display screen together with the bar graph. Therefore, the user can cause the systolic blood pressure average value and/or the diastolic blood pressure average value for the specific time on the specific event occurrence dates to be displayed with a simple operation (that is, operation of selecting the mark representing a specific event and designating a position corresponding to the vertical bar at the specific time).

The first display control unit may display, on the display screen, the systolic blood pressure average value and/or the diastolic blood pressure average value for the specific time on the specific event occurrence dates instead of the systolic blood pressure average value and/or the diastolic blood pressure average value for the specific time over the display target period, or may display, on the display screen, the systolic blood pressure average value and/or the diastolic blood pressure average value for the specific time on the specific event occurrence dates together with the systolic blood pressure average value and/or the diastolic blood pressure average value for the specific time over the display target period.

In the device for displaying blood-pressure-related information according to one embodiment,
the first calculation unit further obtains a systolic blood pressure average value and/or a diastolic blood pressure average value for the specific time on remaining days in which the specific event occurrence dates are excluded from the display target period, and
the first display control unit displays, on the display screen, the systolic blood pressure average value and/or the diastolic blood pressure average value obtained for the specific time on the remaining days together with the systolic blood pressure average value and/or the diastolic blood pressure average value for the specific time on the specific event occurrence dates.

Assuming that the remaining days are k days (k=n−m) within the display target period (n days with n as a natural number) and the systolic blood pressure values at the specific time on the remaining days are BP1R, BP2R, . . . , and BPkR, the "blood pressure average value" for a specific time on the remaining days is defined by (BP1R+BP2R+ . . . +BPkR)/k (in the present embodiment, this definition is extended to the case of k=1). In a case of k=0, since there is no remaining day, the blood pressure average value on the remaining day is not calculated nor displayed.

In the device for displaying blood-pressure-related information of this one embodiment, the first calculation unit further obtains a systolic blood pressure average value and/or a diastolic blood pressure average value for the specific time on remaining days in which the specific event occurrence dates are excluded from the display target period. The first display control unit displays, on the display screen, the systolic blood pressure average value and/or the diastolic blood pressure average value obtained for the specific time on the remaining days together with the systolic blood pressure average value and/or the diastolic blood pressure average value for the specific time on the specific event occurrence dates. This allows the user to know the systolic blood pressure average value and/or the diastolic blood pressure average value for the specific time on the specific event occurrence dates and the systolic blood pressure average value and/or the diastolic blood pressure average value for the specific time on the remaining days in comparison on the display screen.

In the device for displaying blood-pressure-related information according to one embodiment,
the data input unit inputs, together with the blood pressure value data, data of a pulse rate measured together with the systolic blood pressure value and the diastolic blood pressure value, and
the first display control unit displays a change in a pulse rate over the display target period as a line graph along the bar graph on the display screen.

In the device for displaying blood-pressure-related information of this one embodiment, the data input unit inputs, together with the blood pressure value data, data of a pulse rate measured together with the systolic blood pressure value and the diastolic blood pressure value. The first display control unit displays a change in the pulse rate over the display target period as a line graph along the bar graph on the display screen. Here, the pulse rate indicates a rest level (a level whether to be in a resting state or to be in a moving state) of the subject at the time of blood pressure measurement. Therefore, the user can intuitively judge whether or not a change in a blood pressure value over the display target period indicated by the bar graph is due to the rest level of the subject.

In the device for displaying blood-pressure-related information according to one embodiment,
the vertical bars constituting the bar graph are displayed with distinguished by at least any of color, line type, and thickness for each daily time corresponding to each of the vertical bars.

A "line type" refers to, for example, a solid line, a broken line, a one-dot chain line, a two-dot chain line, a double line, and the like, but is not limited to this.

In the device for displaying blood-pressure-related information of this one embodiment, the vertical bars constituting the bar graph are displayed with distinguished by at least any of color, line type, and thickness for each daily time corresponding to each of the vertical bars. Therefore, the user can easily identify the vertical bars constituting the bar graph on the display screen for each daily time corresponding to the each of the vertical bars.

In the device for displaying blood-pressure-related information according to one embodiment,
the pointing device includes a touchpad superimposed on the display screen, and
when operation of pinch out or pinch in is performed in a horizontal direction with the touchpad on the display screen, the initial display control unit changes the display target period by enlarging or reducing display in the horizontal direction of the display screen.

In the device for displaying blood-pressure-related information of this one embodiment, the user performs, on the display screen, operation of pinch out or pinch in in the horizontal direction with the touchpad. Then, the initial display control unit changes the display target period by enlarging or reducing display in the horizontal direction of the display screen. Therefore, the user can change the display target period with simple operation (that is, operation of pinch out or pinch in).

The device for displaying blood-pressure-related information according to one embodiment further comprises:
a second calculation unit that, during display of the bar graph, averages data of the systolic blood pressure value stored in the storage unit over the display target period with putting together the plurality of times to obtain a systolic blood pressure average value for the plurality of times being put together when a position away upward from the bar graph is designated on the display screen with the pointing device, whilst averages data of the diastolic blood pressure value stored in the storage unit over the display target period with putting together the plurality of times to obtain a diastolic blood pressure average value where the plurality of times are put together when a position away downward from the bar graph is designated on the display screen with the pointing device; and
a second display control unit that displays the systolic blood pressure average value or the diastolic blood pressure average value obtained with putting together the plurality of times, together with the bar graph on the display screen.

In the device for displaying blood-pressure-related information of this one embodiment, during display of the bar graph, the user operates the pointing device to designate a position away upward from the bar graph on the display screen. Then, a second calculation unit averages data of the systolic blood pressure value stored in the storage unit over the display target period with putting together the plurality of times to obtain a systolic blood pressure average value for the plurality of times. On the other hand, during display of the bar graph, the user operates the pointing device to designate a position away downward from the bar graph on the display screen. Then, the second calculation unit averages data of the diastolic blood pressure value stored in the storage unit over the display target period with putting together the plurality of times to obtain a diastolic blood pressure average value for the plurality of times. The second display control unit displays the systolic blood pressure average value or the diastolic blood pressure average value obtained with putting together the plurality of times, together with the bar graph on the display screen. Therefore, according to the device for displaying blood-pressure-related information of this one embodiment, the blood pressure average value over the display target period with putting together the plurality of times can be displayed on the display screen with simple operation (that is, operation by the user designating a position away upward or downward from the bar graph on the display screen with the pointing device).

In another aspect, a method for displaying blood-pressure-related information of the present disclosure is a method for displaying blood-pressure-related information for displaying information related to blood pressure of a subject on a display screen, comprising:
  a storage unit that is capable of storing blood pressure value data including a systolic blood pressure value and a diastolic blood pressure value;
  a calculation unit that is capable of calculating the blood pressure value data; and
  a pointing device that is capable of performing operation of designating a position on the display screen,
  the method for displaying blood-pressure-related information comprising:
  receiving, for a subject, the blood pressure value data measured at least at a predetermined plurality of times of a day for each day over a plurality of days, and causing the storage unit to store the blood pressure value data;
  setting date and time in a horizontal direction and blood pressure in a vertical direction on the display screen, and displaying, as a bar graph, a change in a blood pressure value over a display target period corresponding to all or some of the plurality of days with vertical bars each formed by connecting the systolic blood pressure value and the diastolic blood pressure value for each time and arranged in a horizontal direction;
  averaging, when a position corresponding to a vertical bar at a specific time on the display screen is designated with the pointing device during display of the bar graph, data of the systolic blood pressure value measured for each day at the specific time over the display target period to obtain a systolic blood pressure average value for the specific time, and/or averaging data of the diastolic blood pressure value measured for each day at the specific time over the display target period to obtain a diastolic blood pressure average value for the specific time, according to the position designated; and
  displaying, on the display screen, the systolic blood pressure average value and/or the diastolic blood pressure average value obtained for the specific time together with the bar graph.

According to the method for displaying blood-pressure-related information of the present disclosure, the blood pressure average value over a plurality of days (the display target period) for a specific time can be displayed on the display screen with simple operation (that is, operation by the user designating a position corresponding to a vertical bar at a specific time on the display screen with the pointing device).

In yet another aspect, a computer-readable recording medium according to the present disclosure is a non-transitorily computer-readable recording medium storing a program for causing a computer to execute the above method for displaying blood-pressure-related information.

By making a computer read the program stored in the computer-readable recording medium according to the present disclosure and causing a computer to execute the program, the method for displaying blood-pressure-related information can be implemented.

In another aspect, a device for displaying blood-pressure-related information of the present disclosure is a device for displaying blood-pressure-related information that displays information related to blood pressure of a subject on a display screen, the device comprising:
  a data input unit that receives, for a subject, blood pressure value data including a systolic blood pressure value and a diastolic blood pressure value measured at least at a predetermined plurality of times of a day for each day over a plurality of days;
  a storage unit that is capable of storing the blood pressure value data;
  a pointing device that is capable of operation of designating a position on the display screen;
  an initial display control unit that sets date and time in a horizontal direction and blood pressure in a vertical direction on the display screen, and displays a change in a blood pressure value over a display target period corresponding to all or some of the plurality of days as an SBP line graph in which points each corresponding to the systolic blood pressure value are connected by line segments and a DBP line graph in which points each corresponding to the diastolic blood pressure value are connected by line segments;
  a first calculation unit that, when a position corresponding to a specific time on the SBP line graph is designated with the pointing device during display of the line graph, averages data of the systolic blood pressure value measured for each day at a specific time over the display target period to obtain a systolic blood pressure average value for the specific time according to the position designated, and/or, when a position corresponding to a specific time on the DBP line graph is designated with the pointing device during display of the line graph, averages data of the diastolic blood pressure value measured for each day at the specific time over the display target period to obtain a diastolic blood pressure average value for the specific time according to the position designated; and
  a first display control unit that displays, on the display screen, the systolic blood pressure average value and/or the diastolic blood pressure average value obtained for the specific time together with the line graph.

In the device for displaying blood-pressure-related information of the present disclosure, the initial display control unit displays the SBP line graph and the DBP line graph instead of the bar graph described above. During display of the line graph, the user operates the pointing device to designate a position corresponding to a specific time of the SBP line graph. Then, according to the position designated, the first calculation unit averages the data of the systolic blood pressure value measured at the specific time over the display target period to obtain a systolic blood pressure average value for the specific time. Alternatively, during display of the line graph, the user operates the pointing device to designate a position corresponding to a specific time of the DBP line graph. Then, according to the position designated, the first calculation unit averages the data of the diastolic blood pressure value measured at the specific time over the display target period to obtain a diastolic blood pressure average value for the specific time. The first display control unit displays, on the display screen, the systolic blood pressure average value and/or the diastolic blood pressure average value obtained for the specific time together with the line graph. Therefore, according to the device for displaying blood-pressure-related information, the blood pressure average value over a plurality of days (the display target period) at a specific time can be displayed on the display screen with a simple operation (that is, operation by the user designating a position corresponding to a specific time on the line graph with the pointing device).

As known from the above, according to the device for displaying blood-pressure-related information and the method for displaying blood-pressure-related information of the present disclosure, the blood pressure average value over a plurality of days for a specific time can be displayed on the display screen with simple operation. According to the program stored in the computer-readable recording medium of the present disclosure, it is possible to cause a computer to execute such a method for displaying blood-pressure-related information.

The above embodiments are illustrative, and are modifiable in a variety of ways without departing from the scope of this invention. It is to be noted that the various embodiments described above can be appreciated individually within each embodiment, but the embodiments can be combined together. It is also to be noted that the various features in different embodiments can be appreciated individually by its own, but the features in different embodiments can be combined.

The invention claimed is:

1. A device for displaying blood-pressure-related information that displays information related to blood pressure of a subject on a display screen, the device comprising:
   a data input unit that receives, for a subject, blood pressure value data including a systolic blood pressure value and a diastolic blood pressure value measured at least at a predetermined plurality of times of a day for each day over a plurality of days;
   a storage unit that is capable of storing the blood pressure value data;
   a pointing device that is capable of operation of designating a position on the display screen;
   an initial display control unit that sets date and time in a horizontal direction and blood pressure in a vertical direction on the display screen, and displays, as a bar graph, a change in a blood pressure value over a display target period corresponding to all or some of the plurality of days with vertical bars each formed by connecting the systolic blood pressure value and the diastolic blood pressure value for each time and arranged in a horizontal direction;
   a processor configured to act as a first calculation unit that, when a position corresponding to a vertical bar at a specific time on the display screen is designated with the pointing device during display of the bar graph, averages only data of the systolic blood pressure value measured for each day at a same time as the specific time over the display target period to obtain a systolic blood pressure average value for the specific time, and/or averages only data of the diastolic blood pressure value measured for each day at a same time as the specific time over the display target period to obtain a diastolic blood pressure average value for the specific time, according to the position designated; and
   a first display control unit that displays, on the display screen, the systolic blood pressure average value and/or the diastolic blood pressure average value obtained for the specific time together with the bar graph, wherein
   when a position corresponding to an upper end portion of a vertical bar at a specific time on the display screen is designated with the pointing device, the processor acts as the first calculation unit to obtain the systolic blood pressure average value for the specific time according to the position designated, and the first display control unit displays the systolic blood pressure average value obtained for the specific time on the display screen together with the bar graph,
   when a position corresponding to a lower end portion of a vertical bar at a specific time on the display screen is designated with the pointing device, the processor acts as the first calculation unit to obtain the diastolic blood pressure average value for the specific time according to the position designated, and the first display control unit displays the diastolic blood pressure average value obtained for the specific time on the display screen together with the bar graph, and
   when a position corresponding to a central portion of a vertical bar at a specific time on the display screen is designated with the pointing device, the processor acts as the first calculation unit to obtain the systolic blood pressure average value and the diastolic blood pressure average value for the specific time according to the position designated, and the first display control unit displays the systolic blood pressure average value and the diastolic blood pressure average value obtained for the specific time on the display screen together with the bar graph.

2. The device for displaying blood-pressure-related information according to claim 1, wherein
   the first display control unit displays, on the display screen, the systolic blood pressure average value and/or the diastolic blood pressure average value obtained for the specific time as a digital value, and also graphically as a horizontal bar superimposed on the bar graph.

3. The device for displaying blood-pressure-related information according to claim 1, wherein
   the plurality of times include at least two times of a set time and an elapsed time since bedding down.

4. The device for displaying blood-pressure-related information according to claim 1, wherein
   when a position corresponding to one end portion of any of an upper end portion and a lower end portion of the vertical bar at the specific time on the display screen is designated with the pointing device, and then a position corresponding to other end portion of the vertical bar is consecutively designated with the pointing device, the first display control unit displays, on the display screen, a blood pressure average value corresponding to the other end portion for the specific time in addition to a blood pressure average value corresponding to the one end portion for the specific time.

5. The device for displaying blood-pressure-related information according to claim 1, wherein
   when a position corresponding to an upper end portion, a lower end portion, or a central portion of the vertical bar at the specific time on the display screen is designated with the pointing device, and then a position corresponding to a same portion of a vertical bar at another time as that of the vertical bar at the specific time is consecutively designated with the pointing device, the first display control unit displays, on the display screen, a blood pressure average value corresponding to the same portion for the another time in addition to a blood pressure average value corresponding to the upper end portion, the lower end portion, or the central portion for the specific time.

6. The device for displaying blood-pressure-related information according to claim 1, wherein
when a specific position on the display screen is long pressed with the pointing device, the first display control unit increases an amount of information to be displayed together with the bar graph on the display screen as compared with an amount of information to be displayed with short press.

7. The device for displaying blood-pressure-related information according to claim 1, wherein
the initial display control unit displays a mark representing an event that occurred for each day on the subject along the bar graph on the display screen,
when the mark representing a specific event is designated and a position corresponding to the vertical bar at the specific time is designated with the pointing device on the display screen, the processor acts as the first calculation unit to obtain a systolic blood pressure average value and/or a diastolic blood pressure average value for the specific time on specific event occurrence dates on which the specific event occurred, and
the first display control unit display the systolic blood pressure average value and/or the diastolic blood pressure average value obtained for the specific time on the specific event occurrence dates on the display screen together with the bar graph.

8. The device for displaying blood-pressure-related information according to claim 7, wherein
the processor acts as the first calculation unit to further obtain a systolic blood pressure average value and/or a diastolic blood pressure average value for the specific time on remaining days in which the specific event occurrence dates are excluded from the display target period, and
the first display control unit displays, on the display screen, the systolic blood pressure average value and/or the diastolic blood pressure average value obtained for the specific time on the remaining days together with the systolic blood pressure average value and/or the diastolic blood pressure average value for the specific time on the specific event occurrence dates.

9. The device for displaying blood-pressure-related information according to claim 1, wherein
the data input unit inputs, together with the blood pressure value data, data of a pulse rate measured together with the systolic blood pressure value and the diastolic blood pressure value, and
the first display control unit displays a change in a pulse rate over the display target period as a line graph along the bar graph on the display screen.

10. The device for displaying blood-pressure-related information according to claim 1, wherein
the vertical bars constituting the bar graph are displayed with distinguished by at least any of color, line type, and thickness for each daily time corresponding to each of the vertical bars.

11. The device for displaying blood-pressure-related information according to claim 1, wherein
the pointing device includes a touchpad superimposed on the display screen, and
when operation of pinch out or pinch in is performed in a horizontal direction with the touchpad on the display screen, the initial display control unit changes the display target period by enlarging or reducing display in the horizontal direction of the display screen.

12. A device for displaying blood-pressure-related information that displays information related to blood pressure of a subject on a display screen, the device comprising:
a data input unit that receives, for a subject, blood pressure value data including a systolic blood pressure value and a diastolic blood pressure value measured at least at a predetermined plurality of times of a day for each day over a plurality of days;
a storage unit that is capable of storing the blood pressure value data;
a pointing device that is capable of operation of designating a position on the display screen;
an initial display control unit that sets date and time in a horizontal direction and blood pressure in a vertical direction on the display screen, and displays, as a bar graph, a change in a blood pressure value over a display target period corresponding to all or some of the plurality of days with vertical bars each formed by connecting the systolic blood pressure value and the diastolic blood pressure value for each time and arranged in a horizontal direction;
a processor configured to act as a first calculation unit that, when a position corresponding to a vertical bar at a specific time on the display screen is designated with the pointing device during display of the bar graph, averages only data of the systolic blood pressure value measured for each day at a same time as the specific time over the display target period to obtain a systolic blood pressure average value for the specific time, and/or averages only data of the diastolic blood pressure value measured for each day at a same time as the specific time over the display target period to obtain a diastolic blood pressure average value for the specific time, according to the position designated; and
a first display control unit that displays, on the display screen, the systolic blood pressure average value and/or the diastolic blood pressure average value obtained for the specific time together with the bar graph, wherein
when a position corresponding to a vertical bar at a specific time on the display screen is long pressed with the pointing device, the processor acts as the first calculation unit to obtain a systolic blood pressure average value and/or a diastolic blood pressure average value for the specific time over a first half of the display target period, and obtains a systolic blood pressure average value and/or a diastolic blood pressure average value for the specific time over a second half of the display target period, and
the first display control unit displays, on the display screen, the systolic blood pressure average value and/or the diastolic blood pressure average value obtained for the specific time in the first half of the display target period, and the systolic blood pressure average value and/or the diastolic blood pressure average value obtained for the specific time in the second half of the display target period.

13. A device for displaying blood-pressure-related information that displays information related to blood pressure of a subject on a display screen, the device comprising:
- a data input unit that receives, for a subject, blood pressure value data including a systolic blood pressure value and a diastolic blood pressure value measured at least at a predetermined plurality of times of a day for each day over a plurality of days;
- a storage unit that is capable of storing the blood pressure value data;
- a pointing device that is capable of operation of designating a position on the display screen;
- an initial display control unit that sets date and time in a horizontal direction and blood pressure in a vertical direction on the display screen, and displays, as a bar graph, a change in a blood pressure value over a display target period corresponding to all or some of the plurality of days with vertical bars each formed by connecting the systolic blood pressure value and the diastolic blood pressure value for each time and arranged in a horizontal direction;
- a processor configured to act as a first calculation unit that, when a position corresponding to a vertical bar at a specific time on the display screen is designated with the pointing device during display of the bar graph, averages only data of the systolic blood pressure value measured for each day at a same time as the specific time over the display target period to obtain a systolic blood pressure average value for the specific time, and/or averages only data of the diastolic blood pressure value measured for each day at a same time as the specific time over the display target period to obtain a diastolic blood pressure average value for the specific time, according to the position designated; and
- a first display control unit that displays, on the display screen, the systolic blood pressure average value and/or the diastolic blood pressure average value obtained for the specific time together with the bar graph, wherein
- the processor is further configured to act as a second calculation unit that, during display of the bar graph, averages data of the systolic blood pressure value stored in the storage unit over the display target period with putting together the plurality of times to obtain a systolic blood pressure average value for the plurality of times being put together when a position away upward from the bar graph is designated on the display screen with the pointing device, whilst averages data of the diastolic blood pressure value stored in the storage unit over the display target period with putting together the plurality of times to obtain a diastolic blood pressure average value where the plurality of times are put together when a position away downward from the bar graph is designated on the display screen with the pointing device, and
- the device for displaying blood-pressure-related information further comprises a second display control unit that displays the systolic blood pressure average value or the diastolic blood pressure average value obtained with putting together the plurality of times, together with the bar graph on the display screen.

14. A method for displaying blood-pressure-related information for displaying information related to blood pressure of a subject on a display screen, comprising:
- a storage unit that is capable of storing blood pressure value data including a systolic blood pressure value and a diastolic blood pressure value;
- a processor configured to be capable of calculating the blood pressure value data; and
- a pointing device that is capable of performing operation of designating a position on the display screen, the method for displaying blood-pressure-related information comprising:
- receiving, for a subject, the blood pressure value data measured at least at a predetermined plurality of times of a day for each day over a plurality of days, and causing the storage unit to store the blood pressure value data;
- setting date and time in a horizontal direction and blood pressure in a vertical direction on the display screen, and displaying, as a bar graph, a change in a blood pressure value over a display target period corresponding to all or some of the plurality of days with vertical bars each formed by connecting the systolic blood pressure value and the diastolic blood pressure value for each time and arranged in a horizontal direction;
- during display of the bar graph,
    - when a position corresponding to an upper end portion of a vertical bar at a specific time on the display screen is designated with the pointing device, obtaining, by the processor, the systolic blood pressure average value for the specific time according to the position designated, and displaying the systolic blood pressure average value obtained for the specific time on the display screen together with the bar graph,
    - when a position corresponding to a lower end portion of a vertical bar at a specific time on the display screen is designated with the pointing device, obtaining, by the processor, the diastolic blood pressure average value for the specific time according to the position designated, and displaying the diastolic blood pressure average value obtained for the specific time on the display screen together with the bar graph, and
    - when a position corresponding to a central portion of a vertical bar at a specific time on the display screen is designated with the pointing device, the processor acts as a first calculation unit to obtain the systolic blood pressure average value and the diastolic blood pressure average value for the specific time according to the position designated, and the first display control unit displays the systolic blood pressure average value and the diastolic blood pressure average value obtained for the specific time on the display screen together with the bar graph.

15. A non-transitory computer-readable recording medium storing a program for causing a computer to execute the method for displaying blood-pressure-related information according to claim 14.

* * * * *